United States Patent
Hu et al.

(10) Patent No.: US 7,700,607 B2
(45) Date of Patent: Apr. 20, 2010

(54) SUBSTITUTED PYRIDONE COMPOUNDS AND METHODS OF USE

(76) Inventors: Essa Hu, 3824 Fountain St., Camarillo, CA (US) 93012; Jason Brooks Human, 901 Beacon St., Apt. 5, Boston, MA (US) 02215; Roxanne Kunz, 451 San Vicente Blvd., Apt. 11, Santa Monica, CA (US) 90402; Andrew Tasker, 561 Granite Hills St., Simi Valley, CA (US) 93065; Ryan White, 34 Willow Ave., Unit 1, Somerville, MA (US) 02144

( * ) Notice: Subject to any disclaimer, the term of this patent is extended or adjusted under 35 U.S.C. 154(b) by 0 days.

(21) Appl. No.: 11/879,830

(22) Filed: Jul. 18, 2007

(65) Prior Publication Data
US 2008/0249090 A1   Oct. 9, 2008

Related U.S. Application Data

(60) Provisional application No. 60/832,368, filed on Jul. 20, 2006.

(51) Int. Cl.
*A61K 31/517* (2006.01)

(52) U.S. Cl. .................. 514/266.21; 544/111; 544/284; 544/359; 546/171; 546/268.1; 548/235; 548/362.5; 548/375.1; 548/503; 548/561; 549/471

(58) Field of Classification Search ............ 514/266.21; 544/11, 284, 359; 546/171, 268.1; 548/235, 548/362.5, 375.1, 503, 561; 549/471
See application file for complete search history.

(56) References Cited

FOREIGN PATENT DOCUMENTS

| EP | 039051 B1 | 7/1985 |
|---|---|---|
| WO | 0145689 A2 | 6/2001 |
| WO | 03002109 A2 | 1/2003 |
| WO | 2005037285 A1 | 4/2005 |
| WO | 2006039718 A2 | 4/2006 |
| WO | WO 2006/039718 * | 4/2006 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Patani, et al. Chem. Rev., 96, 1996, pp. 3147-3176.*
Kirshenbaum et al., Blood 94:2333-2342, 1999.
Ishizaka et al, Curr. Opinion Immunol. 5:937-943, 1993.
Boissan and Arock, J. Leukoc. Biol. 67:135-148, 2000.
Watanabe et al., Blood 11:3855-3866, 1994.
Yammaguchi et al., Hematology 29:133-139, 1999.
Secor et al., J. Experimental Medicine 191:813-822, 1999.
Andoh et al, Clinical & Experimental Immunology 116:90-93, 1999.
Mauduit et al, Human Rep. Update 5: 535-545, 1999.
Blume-Jensen et al, Nature Genetics 24:157-162, 2000.

* cited by examiner

*Primary Examiner*—James O Wilson
*Assistant Examiner*—Douglas M Willis
(74) *Attorney, Agent, or Firm*—G. Prabhakar Reddy

(57) ABSTRACT

The present invention comprises a new class of compounds capable of modulating the c-kit receptor and, accordingly, useful for treatment of c-kit mediated diseases, including various inflammatory, fibrotic and/or mast cell mediated diseases such as mastocytosis. The compounds have a general Formula I

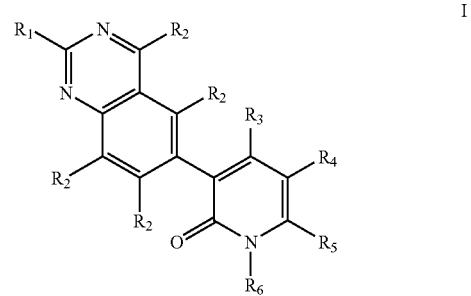

wherein $R^{1-6}$ are defined herein. The invention further comprises pharmaceutical compositions, methods for treatment of c-kit mediated diseases, and intermediates and processes useful for the preparation of compounds of the invention.

4 Claims, No Drawings

SUBSTITUTED PYRIDONE COMPOUNDS AND METHODS OF USE

This application claims the benefit of U.S. Provisional Patent Application No. 60/832,368, filed Jul. 20, 2006, which disclosure is hereby incorporated herein by reference in its entirety.

FIELD OF THE INVENTION

The present invention generally relates to substituted pyridone compounds and their use, including use in pharmaceutical formulations, methods of treatment, and methods of preparing medicaments.

BACKGROUND OF THE INVENTION

C-kit is a receptor tyrosine kinase expressed on the surface of mast cells, to which stem cell factor (SCF) is a ligand. Aberrant c-kit signaling is believed to be a mediator of certain autoimmune diseases. Binding of SCF to the c-kit receptor mediates various functions of the mast cell. As an important mediator of mast cell function, c-kit is thought to also play a role in pathologies associated with mast cells (MC). C-kit functions through mast cell generation, which plays an important role in triggering autoimmune diseases. Mast cells are tissue elements derived from a particular subset of hematopoietic stem cells that express CD34, c-kit and CD13 antigens (Kirshenbaum et al., *Blood* 94:2333-2342, 1999 and Ishizaka et al, *Curr. Opinion Immunol.* 5:937-943, 1993). Mast cells are characterized by their heterogeneity, not only regarding tissue location and structure but also at the functional and histochemical levels (Aldenberg and Enerback, *Histochem. J.* 26:587-596, 1994; Bradding et al., *J. Immunol.* 155:297-307, 1995, Irani et al., *J. Immunol.* 147:247-253, 1991).

Mast cells are thought to participate in the destruction of tissues by releasing various proteases and mediators categorized into three groups: pre-formed granule associated mediators (histamine, proteoglycans, and neutral proteases), lipid-derived mediators (prostaglandins, thromboxanes, and leucotrienes), and various cytokines, including IL-1, IL-2, IL-3, IL-4, IL-5, IL-6, IL-8, TNFα, GM-CSF, MIP-1a, MIP-1b, MIP-2 and IFNγ. The liberation of these mediators induces and activates various components of immune response involved in autoimmune diseases, and also promotes the tissue destruction process.

Activation of the auto-immune response is postulated to be caused by, or stimulated from, the degranulation of mast cells. Immature MC progenitors circulate in the blood stream and differentiate in the tissues. These differentiation and proliferation processes are influenced by various cytokines. Stem Cell Factor (SCF) and IFNγ are two cytokines which are important in influencing such processes. The SCF receptor is encoded by the proto-oncogene c-kit, which belongs to the type III receptor tyrosine kinase subfamily (Boissan and Arock, *J. Leukoc. Biol.* 67:135-148, 2000), along with PDGF and cFMS. Ligation of c-kit receptor by SCF induces its dimerization followed by its transphosphorylation, leading to the recruitment and activation of various intracytoplasmic substrates. IFNγ is another cytokine secreted by mast cells. It has been reported that IFNγ is responsible for major histocompatibility complexes associated with autoimmune diseases (Hooks et al., *New England J. of Med.*, 301:5-8, 1979). These activated substrates induce multiple intracellular signaling pathways responsible for cell proliferation and activation (Boissan and Arock, 2000).

TNF is another cytokine produced by mast cells. More recently, it has been reported that the TNF produced by mast cells is involved in the pathogenesis of auto-antibody mediated vasculitis (Watanabe et al., *Blood* 11:3855-3866, 1994). Mast cells were also shown to control neutrophil recruitment during T-cell mediated delayed-type hypersensitivity reactions through TNF and macrophage inflammatory protein 2 (MIP-2). Accordingly, c-kit regulation may be useful in various types of inflammation including without limitation, rheumatoid arthritis, severe asthma, allergy associated chronic rhinitis, and the like.

Mast cells have also been implicated in liver allograph rejection (Yammaguchi et al., *Hematology* 29:133-139, 1999) and in liver fibrosis, where hepatic stallate cells produce the SCF that recruits the mast cells (Gaca et al., *J. Hematology* 30:850-858, 1999). These observations suggest that c-kit kinase inhibitors may help prevent organ rejection and fibrosis. Some possible related c-kit mediated therapeutic indications include idiopathic pulmonary fibrosis (IPF) and scleroderma. Mast cells have also been implicated in the pathology of multiple sclerosis (Secor et al., *J. Experimental Medicine* 191:813-822, 1999), and ischemia-reperfusion injury (Andoh et al, *Clinical & Experimental Immunology* 116:90-93, 1999) in experimental models using mice with mutant kit receptors that are deficient in mast cells. In both cases, the pathology of the diseases was significantly attenuated relative to mice with normal c-kit and mast cell populations. Thus, the role of mast cells in these diseases suggests that c-kit modulators might be useful therapeutics.

C-kit signaling is also important for fetal gonadal development, and plays a role in adult fertility (Mauduit et al, *Human Rep. Update* 5: 535-545, 1999). Spermatogenesis is inhibited through a reduction of c-kit activity in c-kit signaling through the PI3 kinase pathway (Blume-Jensen et al, *Nature Genetics* 24:157-162, 2000). C-kit expression has been observed to be lower in sub-fertile testes than in normal testicular tissue (Feng et al, *Fertility and Sterility* 71:85-89, 1999). C-kit signaling is also important for oogenesis and folliculogenesis (Parrott and Skinner, *Endocrinology* 140:4262-4271, 1999). These reports suggest that modulation of c-kit enzymatic activity may be a method to reduce both male and female infertility.

While various groups have published on inhibitors of c-kit kinase, disclosing various chemical compounds, including 2-phenylamino-imidazo[4,5-h]isoquinolin-9-ones (Snow, R J et al, *J. Med. Chem.* 2002, 45, 3394), pyrazolo[3,4-d]pyrimidines (Burchat, A F et al, *Bioorganic and Med. Chem. Letters* 2002, 12, 1987 and Hanke, J H et al, J. *Biol. Chem.* 1996, 271, 695), pyrrolo[2,3-d]pyrimidines (Altmann, E et al, *Bioorganic and Med. Chem. Letters* 2001, 11, 853), anilino-quinazolines (Wang, Y D et al, *Bioorganic and Med. Chem. Letters* 2000, 10, 2477), imidazoquinoxalines (Chen, P. et al, *Bioorganic and Med. Chem. Letters* 2002, 12, 3153), PCT publication entitled, "Methods of Modulating C-kit Tyrosine Protein Kinase Function with Indoline Compounds" and PCT publication entitled, "Use of Tyrosine Kinase Inhibitors for Treating Autoimmune Diseases", none of these groups describe the compounds of the present invention, and particularly as modulators of kinase enzymes such as c-kit, and useful for the regulation of autoimmune disease(s), allergies, asthma, cancer and the like.

BRIEF DESCRIPTION OF EXEMPLARY EMBODIMENTS OF THE INVENTION

The compounds of the present invention, including stereoisomers, tautomers, solvates, pharmaceutically acceptable salts and derivatives, and prodrugs thereof, are represented by general Formula I:

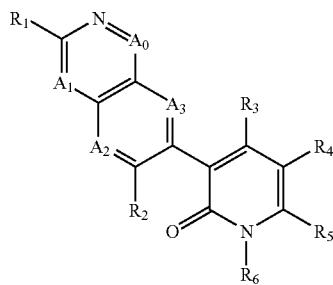

I wherein $A^{0-3}$ and $R^{1-6}$ are defined in the Detailed Description section hereinbelow.

The compounds of Formula I are capable of modulating the activity of c-kit protein kinase and, therefore, are capable of regulating various c-kit related disorders. More specifically, these compounds are useful in the treatment, including preventative, prophylactic and therapeutic treatment, of c-kit kinase-associated or mediated disorders including, but not limited to, mast cell regulated autoimmune disorders and fibrotic disease. In one embodiment of the invention, the compounds of Formula I are useful for the treatment of mast cell production, tumors related to mast cell proliferation and mastocytosis, allergic reactions and c-kit mediated fibrotic and autoimmune disease.

To treat patients for such disorders, another embodiment of the invention provides a pharmaceutical composition comprising a compound of Formula I and a pharmaceutically acceptable carrier. Such a composition can be administered to the subject, such as a human, for the purpose of treating the disorder. Other therapeutic agents such as those described below may be employed in combination with the inventive compounds, such as in a combined composition, administered to the subject. Alternatively, such other therapeutic agent(s) may be administered prior to, simultaneously with, or following the administration of the compound(s) of the present invention.

The foregoing merely summarizes certain aspects of the invention and is not intended, nor should it be construed, as limiting the invention in any way.

DETAILED DESCRIPTION OF THE EXEMPLARY EMBODIMENTS OF THE INVENTION

In one embodiment, the present invention provides a compound of Formula I

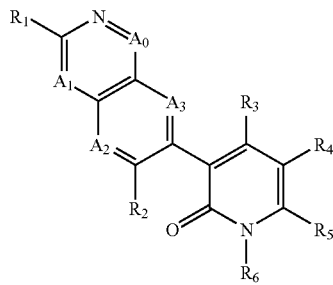

I or stereoisomer, tautomer, solvate, pharmaceutically acceptable salt, derivative or prodrug thereof, wherein each of $A^0$, $A^1$, $A^2$ and $A^3$, independently, is $CR^2$ or N;

$R^1$ is —$NR^7R^7$, —$NR^7R^8$, —$NR^9R^9$, —$C(O)NR^7$, —$C(O)NR^9$, —$NR^2C(O)R^7$, —$NR^2C(O)R^9$, —$NR^2C(O)NR^7$, —$NR^2C(O)NR^9$, —$S(O)_2NR^7$, —$S(O)_2NR^9$ or —$NR^2S(O)_2NR^7$; or $R^1$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

each $R^2$, independently, is H, halo, haloalkyl, $NO_2$, $C_{1-8}$alkyl, $C_{2-8}$alkenyl, $C_{2-8}$alkynyl, CN, OH, —O—$C_{1-8}$alkyl, —O-haloalkyl, SH, —S—$C_{1-8}$alkyl, $NH_2$, —NH—$C_{1-8}$alkyl, —N—$(C_{1-8}alkyl)_2$ or —$C(O)$—$C_{1-8}$alkyl, wherein the $C_{1-8}$-alkyl, $C_{2-8}$-alkenyl and $C_{2-8}$-alkynyl optionally comprising 1-4 heteroatoms selected from N, O and S and optionally substituted with one or more substituents of $R^9$;

$R^3$, at each occurrence, is H, halo, haloalkyl, $NO_2$, $C_{1-8}$alkyl, $C_{2-8}$alkenyl, $C_{2-8}$alkynyl, CN, OH, —O—$C_{1-8}$alkyl, —O-haloalkyl, SH, —S—$C_{1-8}$alkyl, $NH_2$, —NH—$C_{1-8}$alkyl, —N—$(C_{1-8}alkyl)_2$ or —$C(O)$—$C_{1-8}$alkyl, wherein the $C_{1-8}$-alkyl, $C_{2-8}$-alkenyl and $C_{2-8}$-alkynyl optionally comprising 14 heteroatoms selected from N, O and S and optionally substituted with one or more substituents of $R^9$;

$R^4$ is H, $C_{1-8}$alkyl, $C_{2-8}$alkenyl, $C_{2-8}$alkynyl, halo, haloalkyl or CN;

$R^5$ is H, $C_{1-8}$alkyl, $C_{2-8}$alkenyl, $C_{2-8}$alkynyl, halo, haloalkyl or CN;

$R^6$ is $C(O)R^7$, $COOR^7$, $C(O)NR^7R^7$, $C(O)NR^7R^8$, $S(O)_2R^7$, $S(O)_2NR^7R^7$, $S(O)_2NR^7R^8$, $C_{1-10}$-alkyl, $C_{2-10}$-alkenyl or $C_{2-10}$-alkynyl, each of the $C_{1-10}$-alkyl, $C_{2-10}$-alkenyl and $C_{2-10}$-alkynyl optionally comprising 14 heteroatoms selected from N, O and S and optionally substituted with one or more substituents of $R^8$ or $R^9$; or $R^6$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^7$ is H, $C_{1-8}$-alkyl, $C_{2-8}$-alkenyl, $C_{2-8}$-alkynyl, $C_{3-8}$-cycloalkyl or $C_{4-8}$-cycloalkenyl, each of the $C_{1-8}$-alkyl, $C_{2-8}$-alkenyl, $C_{2-8}$-alkynyl, $C_{3-8}$-cycloalkyl and $C_{4-8}$-cycloalkenyl optionally comprising 14 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, OC(O)NR$^9$R$^9$, S(O)$_2$R$^8$, S(O)$_2$NR$^8$R$^9$, S(O)$_2$R$^9$, S(O)$_2$NR$^9$R$^9$, NR$^9$S(O)$_2$NR$^8$R$^9$, NR$^9$S(O)$_2$NR$^9$R$^9$, NR$^9$S(O)$_2$R$^8$, NR$^9$S(O)$_2$R$^9$ or R$^9$;

R$^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of R$^9$, oxo, NR$^9$R$^9$, OR$^9$, SR$^9$, C(O)R$^9$ or a partially or fully saturated or unsaturated 5-6 membered ring of carbon atoms optionally including 1-3 heteroatoms selected from O, N, or S, and optionally substituted independently with 1-3 substituents of R$^9$;

alternatively, R$^7$ and R$^8$ taken together form a saturated or partially or fully unsaturated 5-6 membered ring of carbon atoms optionally including 1-3 heteroatoms selected from O, N, or S, and the ring optionally substituted independently with 1-3 substituents of R$^9$; and R$^9$ is H, halo, haloalkyl, CN, OH, NO$_2$, NH$_2$, acetyl, C$_{1-8}$-alkyl, C$_{2-8}$-alkenyl, C$_{2-8}$-alkynyl, C$_{3-8}$-cycloalkyl, C$_{4-8}$-cycloalkenyl, C$_{1-8}$alkylamino-, C$_{1-8}$-dialkylamino-, C$_{1-8}$-alkoxyl, C$_{1-8}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C$_{1-8}$alkyl, C$_{2-8}$-alkenyl, C$_{2-8}$-alkynyl, C$_{3-8}$-cycloalkyl, C$_{4-8}$-cycloalkenyl, C$_{1-8}$-alkylamino-, C$_{1-8}$-dialkylamino-, C$_{1-8}$-alkoxyl, C$_{1-8}$-thioalkoxyl and ring of said ring system is optionally substituted independently with 1-3 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

In one embodiment, the invention provides compounds wherein A$^1$ is N and A$^0$, A$^2$ and A$^3$, independently, are each CR$^2$, in conjunction with any of the above or below embodiments.

In another embodiment, the invention provides compounds wherein A$^0$ is N and A$^1$, A$^2$ and A$^3$, independently, are each CR$^2$, in conjunction with any of the above or below embodiments.

In another embodiment, the invention provides compounds wherein A$^2$ is N and A$^0$, A$^1$ and A$^3$, independently, are each CR$^2$, in conjunction with any of the above or below embodiments.

In another embodiment, the invention provides compounds wherein A$^3$ is N and A$^0$, A$^1$ and A$^2$, independently, are each CR$^2$, in conjunction with any of the above or below embodiments.

In another embodiment, the invention provides compounds wherein A$^1$ and A$^2$ are each N and A$^0$ and A$^3$ are CR$^2$, in conjunction with any of the above or below embodiments.

In another embodiment, the invention provides compounds wherein A$^1$ and A$^3$ are each N and A$^0$ and A$^2$ are CR$^2$, in conjunction with any of the above or below embodiments.

In another embodiment, the invention provides compounds wherein A$^2$ and A$^3$ are each N and A$^0$ and A$^1$ are CR$^2$, in conjunction with any of the above or below embodiments.

In another embodiment, the invention provides compounds wherein each of A$^0$, A$^1$, A$^2$ and A$^3$, independently, are CR$^2$, in conjunction with any of the above or below embodiments.

In another embodiment, the invention provides compounds wherein each of A$^1$, A$^2$ and A$^3$, independently, are N, in conjunction with any of the above or below embodiments.

In another embodiment, the invention provides compounds wherein R$^1$ is —NR$^7$R$^7$, —NR$^7$R$^8$, —NR$^9$R$^9$, —C(O)NR$^7$, —C(O)NR$^9$, —NR$^2$C(O)R$^7$, —NR$^2$C(O)R$^9$, —NR$^2$C(O)NR$^7$, —NR$^2$C(O)NR$^9$, —S(O)$_2$NR$^7$, —S(O)$_2$NR$^9$ or —NR$^2$S(O)$_2$NR$^7$, in conjunction with any of the above or below embodiments.

In another embodiment, the invention provides compounds wherein R$^1$ is —NR$^7$R$^7$, —NR$^7$R$^8$, —NR$^9$R$^9$, —C(O)NR$^7$, —C(O)NR$^9$, —NR$^2$C(O)R$^7$, —NR$^2$C(O)R$^9$, —S(O)$_2$NR$^7$ or —S(O)$_2$NR$^9$, in conjunction with any of the above or below embodiments.

In another embodiment, the invention provides compounds wherein R$^1$ is H, halo, haloalkyl, CN, OH, NO$_2$, NH$_2$, acetyl, C$_{1-8}$-alkyl, C$_{2-8}$-alkenyl, C$_{2-8}$-alkynyl, C$_{3-8}$-cycloalkyl, C$_{4-8}$-cycloalkenyl, C$_{1-8}$alkylamino-, C$_{1-8}$-dialkylamino-, C$_{1-8}$-alkoxyl or C$_{1-8}$-thioalkoxyl, in conjunction with any of the above or below embodiments.

In another embodiment, the invention provides compounds wherein R$^1$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R$^9$, oxo, NR$^9$R$^9$, OR$^9$, SR$^9$, C(O)R$^9$ or a partially or fully saturated or unsaturated 5-6 membered ring of carbon atoms optionally including 1-3 heteroatoms selected from O, N, or S, and optionally substituted independently with 1-5 substituents of R$^9$, in conjunction with any of the above or below embodiments.

In another embodiment, the invention provides compounds wherein R$^1$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl or cyclohexyl, each of which is optionally substituted independently with 1-5 substituents of R$^9$, in conjunction with any of the above or below embodiments.

In another embodiment, the invention provides compounds wherein R$^1$ is phenyl, pyridyl, pyrimidinyl, triazinyl, pyridazinyl, thiophenyl, furyl, pyrrolyl, pyrazolyl, imidazolyl, triazolyl, thiazolyl, thiadiazolyl, oxazolyl, oxadiazolyl, isoxazolyl or isothiazolyl, each of which is optionally substituted independently with 1-5 substituents of R$^9$, in conjunction with any of the above or below embodiments.

In another embodiment, the invention provides compounds wherein R$^2$ is H, F, Br, Cl, I, CF$_3$, CH$_2$CF$_3$, NO$_2$, C$_{1-8}$alkyl, CN, OH, —OCH$_3$, —OC$_2$H$_5$, —OCF$_3$, NH$_2$, —NH—C$_{1-6}$ alkyl or —N—(C$_{1-8}$alkyl)$_2$, in conjunction with any of the above or below embodiments.

In another embodiment, the invention provides compounds wherein R$^2$ is F, Br, Cl, I, CF$_3$, CN, OH, —OCH$_3$, —OCF$_3$, NH$_2$, methyl, ethyl, propyl, isopropyl, cyclopropyl, butyl, isobutyl, tert-butyl, methylamine, dimethylamine, ethylamine, diethylamine or propylamine, in conjunction with any of the above or below embodiments.

In another embodiment, the invention provides compounds wherein $R^3$ is H, $C_{1-8}$alkylhalo, haloalkyl or CN, in conjunction with any of the above or below embodiments.

In another embodiment, the invention provides compounds wherein $R^3$ is H or haloalkyl, in conjunction with any of the above or below embodiments.

In another embodiment, the invention provides compounds wherein $R^4$ is H, $C_{1-8}$alkyl, $C_{2-8}$alkenyl, $C_{2-8}$alkynyl, halo, haloalkyl or CN, in conjunction with any of the above or below embodiments.

In another embodiment, the invention provides compounds wherein $R^4$ is H or halo, in conjunction with any of the above or below embodiments.

In another embodiment, the invention provides compounds wherein $R^5$ is H, $C_{1-8}$alkyl, $C_{2-8}$alkenyl, $C_{2-8}$alkynyl, halo, haloalkyl or CN, in conjunction with any of the above or below embodiments.

In another embodiment, the invention provides compounds wherein $R^5$ is H or halo, in conjunction with any of the above or below embodiments.

In another embodiment, the invention provides compounds wherein $R^6$ is $C(O)R^7$, $COOR^7$, $C(O)NR^7R^7$, $C(O)NR^7R^8$, $S(O)_2R^7$, $S(O)_2NR^7R^7$, $S(O)_2NR^7R^8$, $C_{1-10}$-alkyl, $C_{2-10}$-alkenyl or $C_{2-10}$-alkynyl, each of the $C_{1-10}$-alkyl, $C_{2-10}$-alkenyl and $C_{2-10}$-alkynyl optionally comprising 1-4 heteroatoms selected from N, O and S and optionally substituted with one or more substituents of $R^8$ or $R^9$, in conjunction with any of the above or below embodiments.

In another embodiment, the invention provides compounds wherein $R^6$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$, in conjunction with any of the above or below embodiments.

In another embodiment, the invention provides compounds wherein $R^6$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl or cyclohexyl, each of which is optionally substituted independently with 1-5 substituents of $R^9$, in conjunction with any of the above or below embodiments.

In another embodiment, the invention provides compounds wherein $R^6$ is phenyl, pyridyl, pyrimidinyl, triazinyl, pyridazinyl, thiophenyl, furyl, pyrrolyl, pyrazolyl, imidazolyl, triazolyl, thiazolyl, thiadiazolyl, oxazolyl, oxadiazolyl, isoxazolyl, isothiazolyl, pyrrolidinyl or pyrazolinyl, each of which is optionally substituted independently with 1-5 substituents of $R^9$, in conjunction with any of the above or below embodiments.

In another embodiment, the invention provides compounds wherein $R^9$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, dihydroindolyl, azaindolyl, isoindolyl, indazolyl, benzofuranyl, dihydrobenzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl or cyclohexyl, each of which is optionally substituted independently with 1-5 substituents, as defined herein, in conjunction with any of the above or below embodiments.

In another embodiment, the invention provides compounds of Formula I wherein $A^1$ is N and each of $A^2$ and $A^3$, independently, is $CR^2$;

$R^1$ is —$NR^7R^7$, —$NR^7R^8$, —$NR^9R^9$, —$C(O)NR^7$, —$C(O)NR^9$, —$NR^2C(O)R^7$, —$NR^2C(O)R^9$, —$NR^2C(O)NR^7$, —$NR^2C(O)NR^9$, —$S(O)_2NR^7$, —$S(O)_2NR^9$ or —$NR^2S(O)_2NR^{77}$;

each $R^2$, independently, is H, F, Br, Cl, I, $CF_3$, $CH_2CF_3$, $NO_2$, $C_{1-8}$alkyl, CN, OH, —$OCH_3$, —$OC_2H_5$, —$OCF_3$, $NH_2$, —NH—$C_{1-6}$alkyl or —N—$(C_{1-8}$alkyl$)_2$;

$R^3$ and $R^4$, at each occurrence, is H, $C_{1-8}$alkyl, halo, haloalkyl or CN; and $R^6$ is a $C_{1-10}$-alkyl or $C_{2-10}$-alkenyl, each of which is optionally substituted with one or more substituents of $R^8$ or $R^9$; or $R^6$ is a phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, dihydrobenzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl or cyclohexyl, each of which is optionally substituted independently with 1-5 substituents of $R^9$, in conjunction with any of the above or below embodiments In another embodiment, the invention provides compounds defined by Formula II

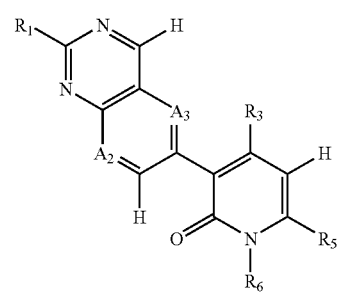

or stereoisomer, tautomer, solvate, pharmaceutically acceptable salt, derivative or prodrug thereof, wherein each of $A^2$ and $A^3$, independently, is $CR^2$ or N;

$R^1$ is —$NR^7R^7$, —$NR^7R^8$, —$NR^9R^9$, —$C(O)NR^7$, —$C(O)NR^9$, —$NR^2C(O)R^7$, —$NR^2C(O)R^9$, —$NR^2C(O)NR^7$, —$NR^2C(O)NR^9$, —$S(O)_2NR^7$, —$S(O)_2NR^9$ or —$NR^2S(O)_2NR^7$; or $R^1$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

each $R^2$, independently, is H, halo, haloalkyl, $NO_2$, $C_{1-8}$alkyl, $C_{2-8}$alkenyl, $C_{2-8}$alkynyl, CN, OH, —O—$C_{1-18}$alkyl, —O-haloalkyl, SH, —S—$C_{1-8}$alkyl, $NH_2$, —NH—$C_{1-8}$alkyl, —N—$(C_{1-8}$alkyl$)_2$ or —C(O)—$C_{1-8}$alkyl, wherein the $C_{1-8}$-alkyl, $C_{2-8}$-alkenyl and $C_{2-8}$-alkynyl optionally comprising 1-4 heteroatoms selected from N, O and S and optionally substituted with one or more substituents of $R^9$;

$R^3$ is H, halo, haloalkyl, $NO_2$, $C_{1-8}$alkyl, CN, OH, —O—$C_{1-8}$alkyl, —O-haloalkyl, SH, —S—$C_{1-8}$alkyl, $NH_2$, —NH—$C_{1-8}$alkyl or —N—$(C_{1-8}$alkyl$)_2$;

$R^5$ is H, $C_{1-8}$alkyl, $C_{2-8}$alkenyl, $C_{2-8}$alkynyl, halo, haloalkyl or CN;

$R^6$ is $C_{1-10}$-alkyl, $C_{2-10}$-alkenyl or $C_{2-10}$-alkynyl, each of the $C_{1-10}$-alkyl, $C_{2-10}$-alkenyl and $C_{2-10}$-alkynyl optionally comprising 1-4 heteroatoms selected from N, O and S and optionally substituted with one or more substituents of $R^8$ or $R^9$; or $R^6$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^7$ is H, $C_{1-8}$-alkyl, $C_{2-8}$-alkenyl, $C_{2-8}$-alkynyl, $C_{3-8}$-cycloalkyl or $C_{4-8}$-cycloalkenyl, each of the $C_{1-8}$-alkyl, $C_{2-8}$-alkenyl, $C_{2-8}$-alkynyl, $C_{3-8}$-cycloalkyl and $C_{4-8}$-cycloalkenyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$ or $R^9$;

$R^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered ring of carbon atoms optionally including 1-3 heteroatoms selected from O, N, or S, and the ring optionally substituted independently with 1-3 substituents of $R^9$; and $R^9$ is H, halo, haloalkyl, CN, OH, $NO_2$, $NH_2$, acetyl, $C_{1-8}$-alkyl, $C_{2-8}$-alkenyl, $C_{2-8}$-alkynyl, $C_{3-8}$-cycloalkyl, $C_{4-8}$-cycloalkenyl, $C_{1-8}$alkylamino-, $C_{1-8}$-dialkylamino-, $C_{1-8}$-alkoxyl, $C_{1-8}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-8}$alkyl, $C_{2-8}$-alkenyl, $C_{2-8}$-alkynyl, $C_{3-8}$-cycloalkyl, $C_{4-8}$-cycloalkenyl, $C_{1-8}$-alkylamino-, $C_{1-8}$-dialkylamino-, $C_{1-8}$-alkoxyl, $C_{1-8}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

In another embodiment, the invention provides compounds of Formula II wherein each of $A^2$ and $A^3$, independently, is CH;

$R^3$ is halo, haloalkyl, $C_{1-8}$alkyl, CN, OH, —O—$C_{1-8}$alkyl, —O-haloalkyl, —NH—$C_{1-8}$alkyl or —N—$(C_{1-8}$alkyl$)_2$;

$R^5$ is H or halo; and $R^6$ is a $C_{1-10}$-alkyl or $C_{2-10}$-alkenyl, each of which is optionally substituted with one or more substituents of $R^8$ or $R^9$; or $R^6$ is a phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, dihydrobenzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl or cyclohexyl, each of which is optionally substituted independently with 1-5 substituents of $R^9$, in conjunction with any of the above or below embodiments.

In many further embodiments of compounds related to Formula II, $A^2$, $A^3$, $R^2$, $R^3$, $R^4$, $R^5$ and $R^6$ are as defined in any of the above embodiments in conjunction with compounds of Formula I hereinabove.

In yet another embodiment, there are provided the compounds of Examples 1-60 described herein, or a pharmaceutically acceptable salt thereof.

The compounds of Formulas I or II, and stereoisomers, solvates, tautomers, pharmaceutically acceptable salts and derivatives, and prodrugs of these compounds, are useful for treating subjects, typically mammals such as humans, with various conditions and/or disease states, as previously described. To this end, and in another embodiment, the invention provides pharmaceutical compositions (also commonly referred to as medicaments, which may be used to treat various conditions or diseases) comprising one or more of the compounds of Formula I or II, including compounds according to any of the various embodiments described above, and a pharmaceutically acceptable carrier or diluent.

The compounds of Formula I or II, or pharmaceutical composition comprising such compound(s), may be administered in an effective amount to the subject to modulate one or more target proteins in the subject thereby treating the target-mediated disease or condition. Accordingly, another embodiment of the invention relates to a method for treating a c-kit kinase-mediated disorder in a mammal, comprising administering to the mammal a therapeutically effective amount of a compound according to any one of the above embodiments.

Further embodiments of the present invention include methods for treating conditions, disorders or diseases related to c-kit, including without limitation, treating the over-production of histamine in a subject, treating an autoimmune disease, mastocytosis, mast cell tumors, asthma, severe asthma, chronic rhinitis, allergy associated chrinic rhinitis, small cell lung cancer, acute myelocytic leukemia, acute lymphocytic leukemia, myelodysplastic syndrome, chronic myelogenus leukemia, colorectal carcinoma, gastric carcinoma, gastrointestinal stromal tumor, testicular cancer, glioblastoma, astrocytoma, fibrotic diseases including without limitation, idiopathic pulmonary fibrosis, or a combination thereof in a subject, wherein each of the above methods, independently, comprise administering to the subject or mammal a therapeutically effective amount, or a therapeutically effective dosage amount, of a compound according to any one of the above embodiments related to Formulas I or II.

Various other embodiments of the invention relate to the manufacture and/or use of a medicament, comprising a compound of Formulas I or II, for the purposes of treating the subject therewith, as described herein. For example, and in another embodiment, the invention relates to the manufacture of, or use of, a medicament comprising a compound according to any one of the above embodiments related to Formulas I or II for the treatment of fibrotic disease.

Another embodiment of the invention relates to a method of making a compound according to Formula I or II, as described herein, comprising the step of reacting a compound of general formula 51

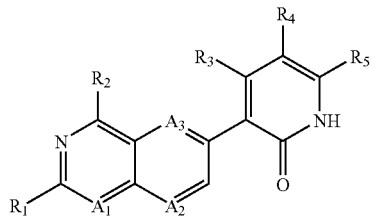

51 wherein $A^1$, $A^2$, $A^3$ and $R^{1-5}$ are as defined herein, with a compound having a general formula 52

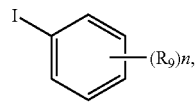

52 wherein $R^9$ and n are as defined herein, in the presence of CuI to make a compound of Formula I.

Meanings And Definitions

Unless otherwise specified, the following terms found in the specification and claims have the following meanings and/or definitions:

aq: Aqueous
ATP: Adenosine triphosphate
BSA: Bovine Serum Albumin
DCE: Dichloroethane
DCM: Dichloromethane
DIEA: Diisopropylethylamine
DMF: N,N-Dimethylformamide
DMSO: Dimethylsulfoxide
EDTA: Ethylene diamine tetraacetic acid
EtOAc: Ethyl acetate
EtOH: Ethanol
g: Gram(s)
h, hr: Hour(s)
HBTU: O-Benzotriazol-1-yl-N,N,N',N'-tetramethyluronium hexafluorophosphate
Hepes: N-[2-Hydroxyethyl]piperazine-N'-[2-ethanesulfonic acid]
$IC_{50}$ value: The concentration of an inhibitor that causes a 50% reduction in a measured activity.
IPA isopropyl alcohol
LiHMDS: Lithium bis(trimethylsilyl)amide
MeI: Methyl iodide
MeCN: Acetonitrile
MeOH: Methanol
min: Minute(s)
mmol: Millimole(s)
NCS: N-chlorosuccinimide
NMP: N-methylpyrrolidone
RT: Room temperature
TFA: Trifluoroacetic acid
THF: Tetrahydrofuran Generally, reference to a certain element such as hydrogen or H is meant to include all isotopes of that element. For example, if an R group is defined to include hydrogen or H, it may also include deuterium and tritium. Compounds comprising radioisotopes such as tritium, $C^{14}$, $P^{32}$ and $S^{35}$ are thus within the scope of the invention. Procedures for inserting such labels into the compounds of the invention will be readily apparent to those skilled in the art based on the disclosure herein.

The term "substituted" as used herein refers to a group, such as those defined below, in which one or more bonds to a hydrogen atom contained therein are replaced by a bond to non-hydrogen or non-carbon atoms including, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfoxide groups, sulfone groups, and sulfonyl groups such as sulfonyl halides and sulfonomides; a nitrogen atom in groups such as amines, amides, alkylamines, dialkylamines, arylamines, alkylarylamines, diarylamines, N-oxides, ureas, imines, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups and others also include groups in which one or more bonds to a carbon(s) or hydrogen(s) atom is replaced by a bond to a heteroatom such as oxygen in carboxylic acid, ester and carbamate groups; and nitrogen in groups such as imines, oximes, hydrazones, and nitriles.

Substituents, including alkyl and ring groups, may be either monovalent or polyvalent depending on the context of their usage. For example, if description contained the group $R^1—R^2—R^3$ and $R^2$ was defined as $C_{1-6}$alkyl, then the $R^2$ alkyl would be considered polyvalent because it must be bonded to at least $R^1$ and $R^3$. Alternatively, if $R^1$ were defined as $C_{1-6}$alkyl, then the $R^1$ alkyl would be monovalent (except any further substitution language).

The term "unsubstituted" as used herein with reference to a group, means that the group does not have one or more bonds to a hydrogen or carbon atom contained therein replaced by a bond to non-hydrogen or non-carbon atom, as described above.

The term "optionally substituted" as used herein with reference to a group, means that the group may be substituted with a specified number of defined substituents or the group may remain unsubstituted. Generally, the scope of the contemplated substitutions of a particular group will be specified.

The term "alkyl" as used herein either alone or within other terms such as "haloalkyl", "alkylamino" and "cycloalkyl", refers to linear, branched or cyclic radicals having one to about twelve carbon atoms. "Cycloalkyl" is also used exclusively herein to refer specifically to fully or partially saturated cyclic alkyl radicals. Examples of "alkyl" radicals include methyl, ethyl, n-propyl, isopropyl, n-butyl, isobutyl, sec-butyl, tert-butyl, pentyl, isoamyl, hexyl, cyclopropyl, cyclopentyl, cyclohexyl and the like.

The term $C_{a\text{-}b}$alkyl" as used herein refers to an alkyl group comprising from a to b carbon atoms in a branched, cyclical or linear relationship or any combination of the three. The alkyl groups described in this section may also contain double or triple bonds. Examples of $C_{1\text{-}8}$alkyl include, but are not limited to the following:

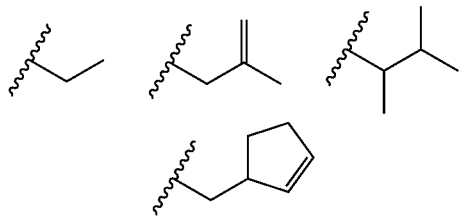

The term "halogen" and "halo" as used herein, refers to a halogen atoms selected from F, Cl, Br and I.

The term "haloalkyl", as used herein refers to radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "perfluoroalkyl" means alkyl radicals having all hydrogen atoms replaced with fluoro atoms. Examples include trifluoromethyl and pentafluoroethyl.

The term "$C_{a\text{-}b}$haloalkyl" as used herein refers to an alkyl group, as described above, wherein any number, and at least one, of the hydrogen atoms attached to the alkyl chain are replaced by F, Cl, Br or I. Examples of haloalkyl includes, without limitation, trifluoromethyl, pentafluoroethyl and the like.

The term "hydroxyalkyl" as used herein refers to linear or branched alkyl radicals having one to about ten carbon atoms any one of which may be substituted with one or more hydroxyl radicals. Examples of such radicals include hydroxymethyl, hydroxyethyl, hydroxypropyl, hydroxybutyl and hydroxyhexyl.

The term "alkoxy" as used herein refers to linear or branched oxy-containing radicals each having alkyl portions of one to about ten carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of lower haloalkoxy radicals having one to three carbon atoms include fluoromethoxy, chloromethoxy, trifluoromethoxy, trifluoroethoxy, fluoroethoxy and fluoropropoxy.

The term "sulfonyl", as used herein whether alone or linked to other terms such as alkylsulfonyl, refers respectively to divalent radicals —$SO_2$—.

The term "amino", as used herein whether alone or linked to other terms, refers to a nitrogen radical containing two hydrogen atoms ($NH_2$), a nitrogen radical which is monosubstituted such as an alkylamine (methylamine for example), or a nitrogen radical which is disubstituted such as a dialkylamine (dimethylamine for example). Generally, the amine nitrogen is the point of attachment to the group in question. Accordingly, the term "alkylamino" or dialkylamino" as used herein, means a mono-alkyl or bis-alkyl substituted amine-linked group. The term "cycloalkylamino" refers to an amine-linked cycloalkyl group. The term "arylamino" refers to an amine-linked aryl group. The term "heteroarylamino" refers to an amine-linked heteroaryl group. The term "heterocyclylamino" refers to an amino-linked heterocyclyl group.

The phrase "partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S" as used herein, means each ring of the single, double or triple ring radical or ring system (fused ring radical in the case of a double or triple) may be a carbocyclic ring ("cycloalkyl"), an aromatic carbocycle (an "aryl" group), a heterocyclic ring or a heteroaromatic ring (a "heteroaryl" ring), each of which is optionally substituted as specified.

The term "aryl", as used herein alone or in combination, refers to a carbocyclic aromatic system containing one, two or three rings wherein such rings may be attached together in a fused manner. The term "aryl" includes, without limitation, aromatic radicals such as phenyl, naphthyl, indenyl, tetrahydronaphthyl, and indanyl. The "aryl" group may have 1 to 3 substituents such as alkyl, hydroxyl, halo, haloalkyl, nitro, cyano, alkoxy and alkylamino. "Aryl" also includes the moiety wherein the aromatic carbocycle is fused with a $C_{3\text{-}6}$cycloalkyl bridge, wherein the bridge optionally includes 1, 2 or 3 heteroatoms selected from N, O and S. For example, phenyl substituted with —O—$CH_2$—O— forms the aryl benzodioxolyl substituent.

The term "heterocyclic" as used herein, refers to fully or partially saturated heteroatom-containing ring radicals, where the heteroatom(s) may be selected from nitrogen, sulfur and oxygen.

The term "heterocycloalkyl" as used herein, refers to saturated and partially saturated (or partially unsaturated) heteroatom-containing ring radicals, where the heteroatoms may be selected from nitrogen, sulfur and oxygen. It does not include rings containing —O—O—, —O—S— or —S—S— portions. Said "heterocycloalkyl" group may have 1 to 3 substituents such as hydroxyl, Boc, halo, haloalkyl, cyano, lower alkyl, oxo, alkoxy, amino and alkylamino.

Examples of saturated heterocycloalkyl radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heteroaryl" as used herein, refers fully unsaturated heteroatom-containing ring radicals, where the heteroatoms may be selected from nitrogen, sulfur and oxygen. Examples of heteroaryl radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heteroaryl" also embraces radicals where heterocyclic radicals are fused/condensed with aryl radicals (also referred to herein as "arylheterocycloalkyl"): unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Further examples of suitable heterocycles and heteroaryls, some of which have been described above, include, without limitation, the following:

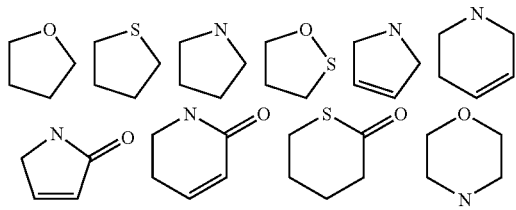

-continued

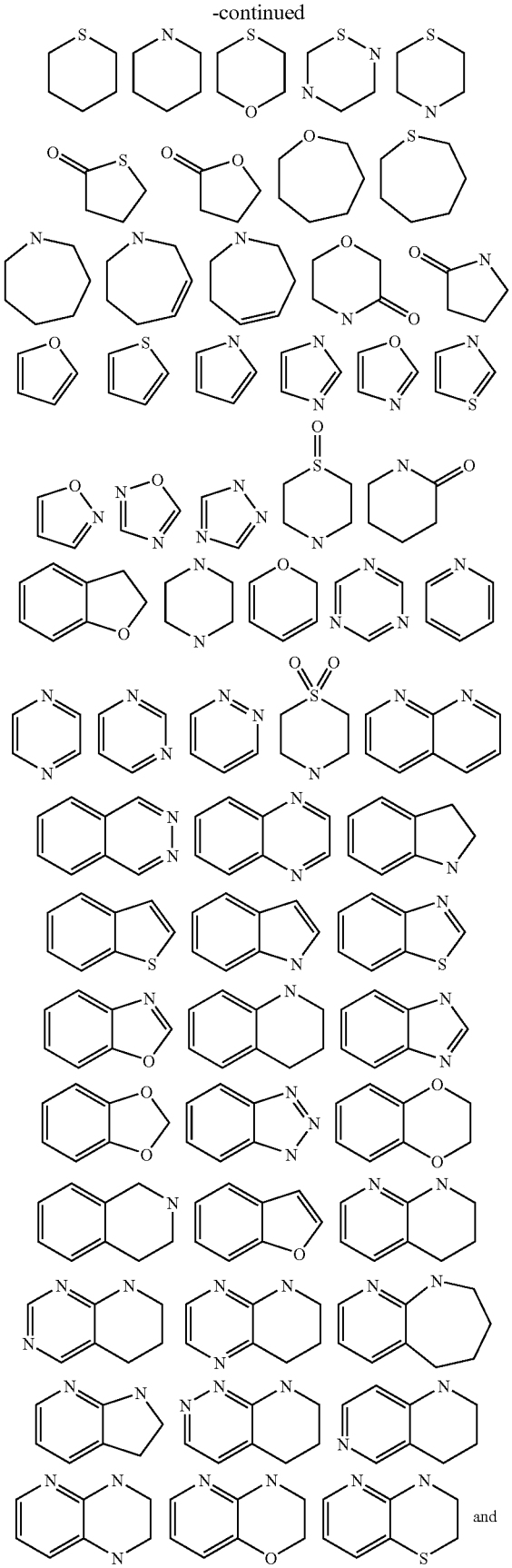

and

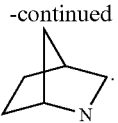

"Saturated or unsaturated" means a moiety or substituent that is completely saturated, completely unsaturated, or has any degree of unsaturation therein. Examples of a saturated or unsaturated 6-membered ring carbocycle would include phenyl, cyclohexyl, cyclohexenyl and cyclohexadienyl.

The term "salt" refers to a salt form of a free base compound of the present invention, as appreciated by persons of ordinary skill in the art. Salts may be prepared by conventional means, known to those skilled in the art. The term "pharmaceutically-acceptable", when used in reference to a salt, refers to salt forms of a given compound, which are within governmental regulatory safety guidelines for ingestion and/or administration to a subject. The term "pharmaceutically-acceptable salts" embraces salts commonly used to form alkali metal salts and to form addition salts of free acids or free bases. The nature of the salt is not critical, provided that it is safe and considered pharmaceutically-acceptable.

Suitable pharmaceutically-acceptable acid addition salts of compounds of Formulas I-II may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of compounds of Formulas I-II include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine.

Additional examples of such acid and base addition salts can be found in Berge et al., J. Pharm. Sci., 66, 1 (1977). All of these salts may be prepared by conventional means from the corresponding compound of the invention by reacting, for example, the appropriate acid or base with the compound of Formulas I-II.

Also, the basic nitrogen-containing groups of compounds of Formulas I-II can be quaternized with such agents as lower alkyl halides including, without limitation, methyl, ethyl, propyl, and butyl chloride, bromides and iodides; dialkyl sulfates including dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products may be obtained by quaternizing such basic nitrogen groups in compounds of Formulas I-II.

The term "derivative" as used herein, refers to simple modifications, readily apparent to those of ordinary skill in the art, on the parent core structure of Formulas I or II, which does not significantly affect (generally decrease) the activity of the compound in-vitro as well as in vivo, in a subject. The term, "derivative" as used herein, is contemplated to include pharmaceutically acceptable derivatives of compounds of Formulas I or II.

The term "pharmaceutically acceptable" when used with reference to a derivative, is consistent in meaning with reference to a salt, and refers to a derivative that is pharmacologically safe for consumption, generally as determined by a governmental or authorized regulatory body.

The term "leaving group" as used herein, refers to groups readily displaceable by a nucleophile, such as an amine, a thiol or an alcohol nucleophile. Leaving groups are well known in the art. Examples of leaving groups include, but are not limited to, N-hydroxysuccinimide, N-hydroxybenzotriazole, halides, triflates, tosylates and the like. Preferred leaving groups are indicated herein where appropriate.

The term "protecting group" as used herein, refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl (also known as arylalkyl), substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups, including aralkyl groups for example, are also suitable for protecting carboxy, hydroxy and mercapto groups. Alkyl groups are also suitable groups for protecting hydroxy and mercapto groups, such as tert-butyl.

Silyl protecting groups are groups containing silicon atoms which are optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis (dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

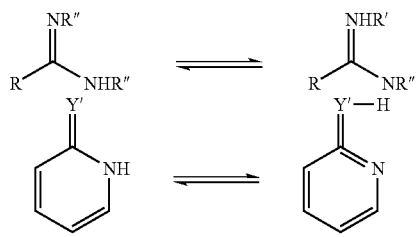

-continued

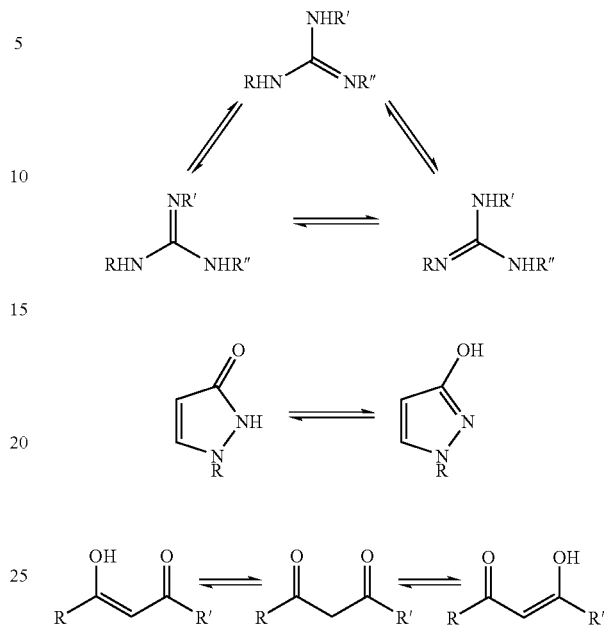

and though one form is named, described, displayed and/or claimed herein, all the tautomeric forms are intended to be inherently included in such name, description, display and/or claim.

Prodrugs of the compounds of this invention are also contemplated by this invention. The term "prodrug", as used herein, refers to a compound, which when administered to the body of a subject (such as a mammal), breaks down in the subject's metabolic pathway to provide an active compound of Formulas I or II. More specifically, a prodrug is an active or inactive "masked" compound that is modified chemically through in vivo physiological action, such as hydrolysis, metabolism and the like, into a compound of this invention following administration of the prodrug to a subject or patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985).

One common form of a prodrug is a masked carboxylic acid group. Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as phosphates, esters and ethers. EP 039,051 (Sloan and Little, Apr. 11, 1981) discloses Mannich-base hydroxamic acid prodrugs, their preparation and use.

Steroeisomers of the compounds of the present invention are also contemplated herein. The term "stereoisomer" as used herein refers to a compound having one or more asymmetric centers. Chiral centers in a compound generally cause that compound to exist in many different conformations or stereoisomers. The term "stereoisomers" includes enantiomers, diastereomers, atropisomers and geometric isomers. Stereoisomers generally possess different chemical properties and/or biological activity, as appreciated by those skilled in the art. For example, one stereoisomer may be more active and/or may exhibit beneficial effects in comparison to other stereoisomer(s) or when separated from the other stereoisomer(s). However, it is well within the skill of the ordinary artisan to separate, and/or to selectively prepare said stereoisomers. Accordingly, "stereoisomers" of the present invention necessarily include mixtures of stereoisomers, including racemic mixtures, individual stereoisomers, and optically active forms.

The term "solvate" when used with reference to a compound refers to a compound, which is associated with one or more molecules of a solvent, such as an organic solvent, inorganic solvent, aqueous solvent or mixtures thereof. The compounds of Formulas I or II may also be solvated, especially hydrated. Hydration may occur during manufacturing of the compounds or compositions comprising the compounds, or the hydration may occur over time due to the hygroscopic nature of the compounds. Compounds of the invention may exist as organic solvates as well, including DMF, ether, and alcohol solvates among others. The identification and preparation of any particular solvate is within the skill of the ordinary artisan of synthetic organic or medicinal chemistry.

The term "treatment" as used herein, includes therapeutic treatment as well as prophylactic treatment (either preventing the onset of disorders altogether or delaying the onset of a pre-clinically evident stage of disorders in individuals).

The term "therapeutically-effective" as used herein, is intended to qualify the amount of each compound of Formulas I or II, which will achieve the goal of treatment, for example, improvement in disorder severity and the frequency of incidence over treatment of each agent by itself, while avoiding adverse side effects typically associated with alternative therapies.

The term "c-kit-mediated disease or disease states" refer to all disease states wherein C-kit plays a role, either directly as c-kit itself, or by c-kit inducing or mediating other proteins, cytokines, enzymes or disease-causing agents and the like to be released, activated or otherwise directly or indirectly regulated.

The specification and claims contain a listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups from the genus.

1. Synthesis

Compounds of Formula I and II can be synthesized according to one or more of the following schematic procedures and specific methods wherein the substituents are as defined for Formulas I and II, above, except where further noted. The procedures and methods as shown relate to preparation of compounds having unspecified stereochemistry. However, such procedures and methods may generally be applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion. Compounds and examples taught herein are either named with conventional IUPAC naming system or with the naming system utilized in ChemDraw, software version 8.0.

2. Scheme 1

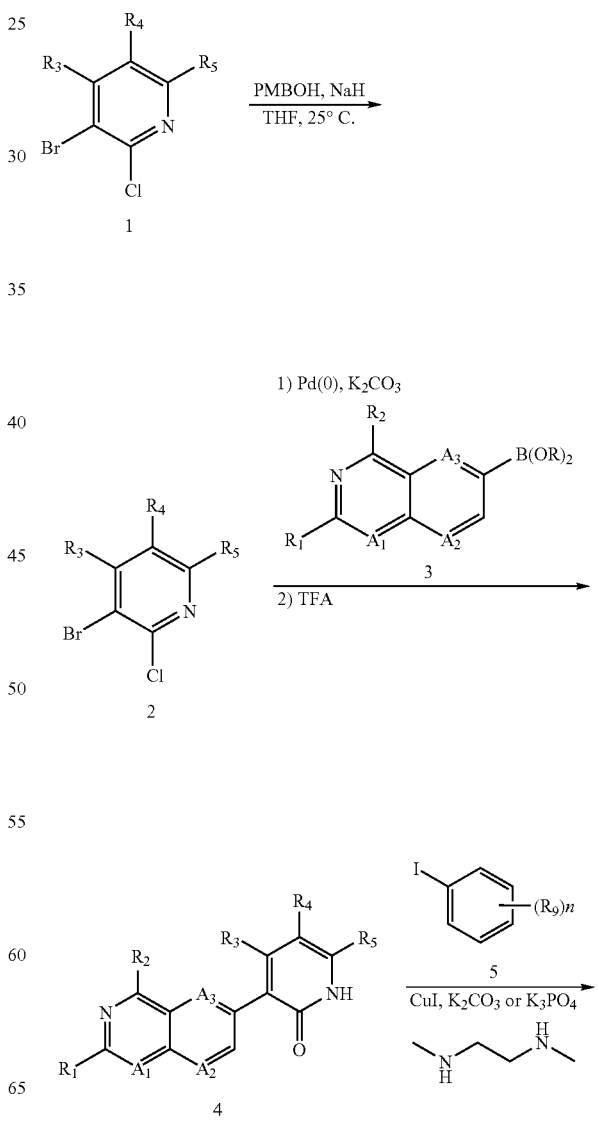

-continued

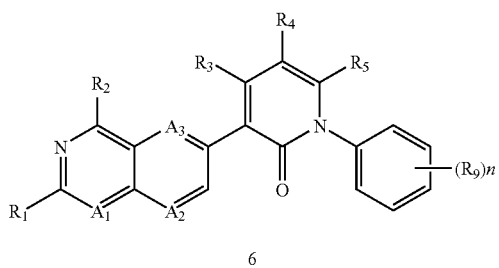

6

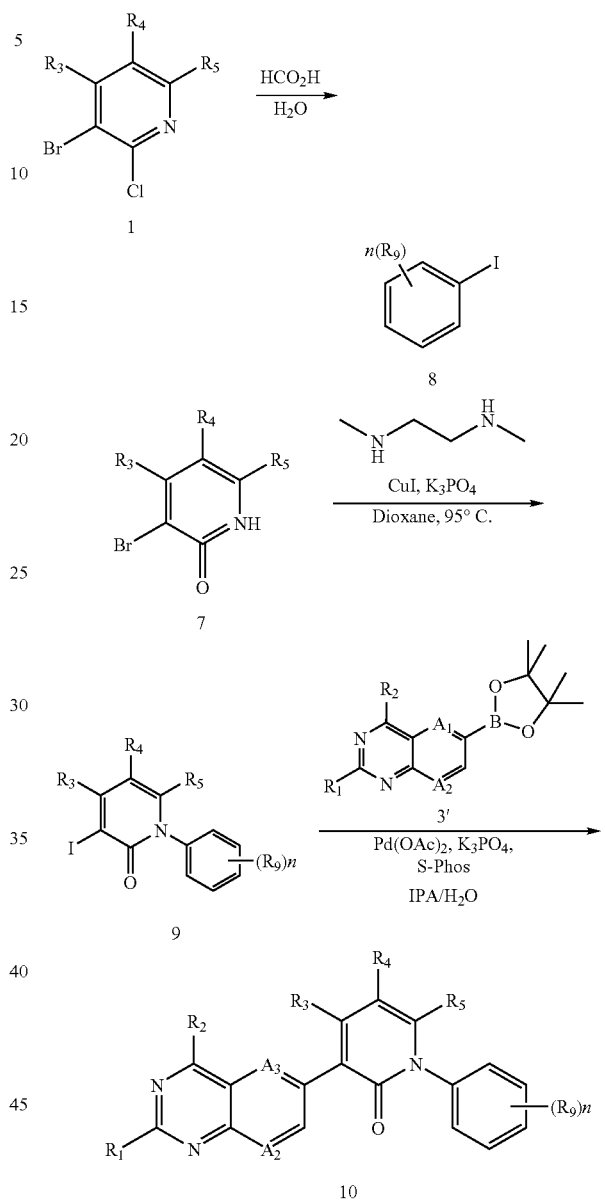

Scheme 1 describes a general method for preparing heteroaryl, aryl substituted pyridone compounds 6, of Formulas I and II. As shown, a desirable chloro, bromo-substituted pyridine 1 can be treated with p-methoxybenzyl (PMB) alcohol, in the presence of a strong base, such as NaH, under suitable conditions to provide the corresponding PMB-protected alcohol intermediate 2. The bromide of compound 2 may be reacted in a Suzuki-like fashion under Suzuki or comparable Suzuki-like conditions, as discussed later herein, with an aryl boronic acids or boronate ester reagent/starting material 3, using a suitable base such as a carbonate base, in the presence of a suitable solvent, such as toluene, to generate the corresponding aryl-coupled adduct (not shown). Aryl boronic acids such as compound 3 may be made using procedures described in PCT application WO 2006039718A2, which is incorporated herein by reference in its entirety. Schemes 3-5 herein also describe how such aryl boronic acids 3 may be made and couples in a Suzuki-like manner to a pyridone compound. This intermediate can be treated with an acid, such as TFA, sufficient to remove the alcohol protecting group, affording the pyridone compound 4. The pyridone 4 can be converted to the corresponding desired compound 6, using a variety of known methods, such as with cuprate chemistry, as shown. The iodide material 5 can be reacted with pyridone 4 in the presence of CuI and a suitable base and solvent, to afford the desired compounds 6. While the aryl iodide 5 is shown as a phenyl ring, the invention is not so limited, and other aryl or heteroaryl $R^6$ groups are also contemplated herein.

The Suzuki method is a reaction using a borane reagent, such as a dioxaborolane intermediate 3 and a suitable leaving group containing reagent, such as the LG-pyridine compound 2 (LG=X=I, Br, Cl). As appreciated to one of ordinary skill in the art, Suzuki reactions also use palladium as a catalyst, in the presence of a suitable base, such as a carbonate base, bicarbonate or an acetate base, in a suitable solvent, such as toluene, acetonitrile, DMF or an aqueous-organic solvent combination or a biphasic system of solvents. Suitable palladium reagents include $Pd(PPh_3)_4$, $Pd(OAc)_2$ or $Pd(dppf)Cl_2$. Where LG is a halide, the halide may be an iodide, a bromide or even a chloride (chloro-pyridyl or chloro-picolinyl rings undergo suzuki reactions in the presence of $Pd(OAc)_2$). Other LGs are also suitable. For example, Suzuki couplings are known to occur with a sulfonate, such as trifluoromethanesulfonate, as the leaving group.

Scheme 2 describes a general method for preparing heteroaryl, aryl substituted pyridone compounds 10, of Formulas I and II. As shown, a desirable chloro, bromo-substituted pyridine 1 can be hydrolyzed with aqueous formic acid to provide the corresponding bromo-pyridone compound 7. Compound 7 may be reacted with desired $R^6$ groups, such as the desirably substituted phenyl as shown, in the presence of CuI and a suitable base and solvent, to generate the iodo-intermediate 9. Compound 9 can be coupled with a desired heteroaryl, such as a quinazoline (above where $A^2$ and $A^3$ are both CH) under Suzuki or comparable Suzuki-like conditions, such as $Pd(OAc)_2$ and potassium phosphate, with an aryl boronic acid reagent/starting material 3' to generate the corresponding heteroaryl, aryl substituted pyridone compounds 10.

Scheme 3

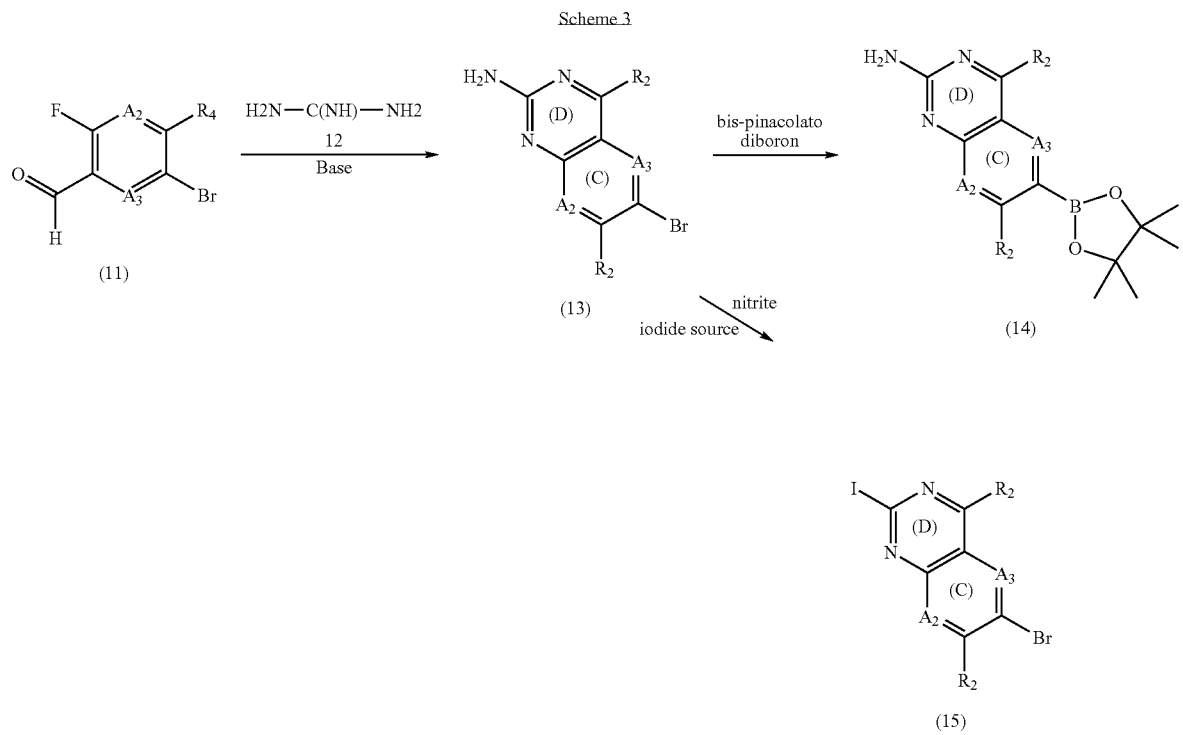

A 2-amino-6-halo or boron substituted-aryl nitrogen-containing bicyclic ring 13 or 14, respectively, a quinoline where one of the nitrogens on the ring is carbon (not shown), a quinazoline ring system where $A^2$ and $A^3$ are both carbon, an aza-quinazoline ring system where either of $A^2$ or $A^3$ are nitrogen or a diaza-quinazoline ring system where both of $A^2$ or $A^3$ are nitrogen, and which are generally referred to herein as the C-D ring portion of the compounds of Formulas I and II, can be prepared according to the method generally described in Scheme 3. As shown, a halo-arylcarboxaldehyde 11 can be treated with guanidine 12 in the presence of a suitable solvent and a mild base, such as a tertiary amine base such as DIEA and/or NMP, to form the 2-amino-6-bromo nitrogen-containing bicyclic ring 13. 2-amino-6-bromo nitrogen-containing bicyclic ring 13 can then be treated with bis (pinacolato)diboron to form the corresponding 6-dioxaborolane 14. Alternatively, the 2-amino of compound 13 can be converted to the corresponding 2-iodo shown in compound 15, by first transforming the $NH_2$ to the corresponding diazonium intermediate (not shown). The diazonium ion can then be replaced by addition of an iodide ion, provided from a suitable iodide source such as iodine or diiodomethane. The reaction occurs by initial elimination of the diazide cation followed by addition of the iodide anion in $S_N1$ mechanistic fashion. Compound 13 where $R^2$ is $NH_2$ and $A^2$ is N can be prepared using a method described in *J. Med. Chem.* 40, 470, 1997. The bromide 13, the boron compound 14 and iodo compound 15 are useful intermediates for coupling to desirably substituted or unsubstituted pyridones, as illustrated in Formulas I and II.

Scheme 4

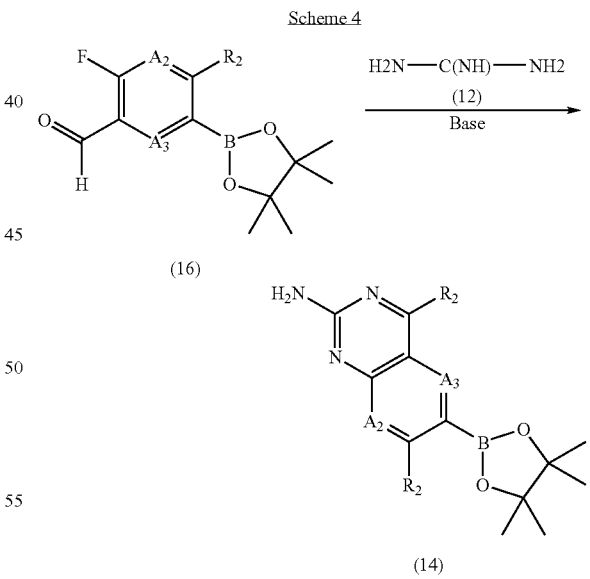

Alternatively, 2-amino-6-dioxaborolan-2-yl-aryl nitrogen-containing bicyclic ring 14, can be prepared according to the method generally described in Scheme 2. As shown, a 2-halo-5-(4,4,5,5-tetramethyl-1,2,3-diboroxalan-2-yl) arylcarboxaldehyde 16 can be treated with guanidine 12 in the presence of a suitable solvent under suitable heat, such as in a microwave reactor, to form the 2-amino-6-dioxaborolane nitrogen-containing bicyclic ring 14.

The methods of Schemes 3-4 also readily apply to synthesis of the 4-NH$_2$ substituted quinazolines, aza-quinazolines and diazaquinazolines, as appreciated by the skilled artisan.

The Specific Methods and Examples described in detail below further exemplify the synthesis of compounds of Formulas I and II, generally described in Schemes 1 and 2 above.

Analytical Methods:

Unless otherwise indicated all HPLC analyses were run on an HP-1000 or HP-1050 system with an HP Zorbax SB-C$_{18}$ (5μ) reverse phase column (4.6×150 mm) run at 30° C. with a flow rate of 1.00 mL/min. The mobile phase used solvent A (H$_2$O/0.1% TFA) and solvent B (CH$_3$CN/0.1% TFA) with a 20 min gradient from 10% to 90% CH$_3$CN. The gradient was followed by a 2 min return to 10% CH$_3$CN and a 3 min flush.

LC-MS Methods:

Unless otherwise noted, the LC-MS analysis of exemplary compounds, intermediates and starting materials described here were conducted using one or both of the following two methods:

Method A:

Samples were run on an HP-1100 system with an HP Zorbax SB-C$_8$ (5μ) reverse phase column (4.6×50 mm) run at 30° C. with a flow rate of 0.75 mL/min. The mobile phase used solvent A (H$_2$O/0.1% HCO$_2$H) and solvent B (CH$_3$CN/ 0.1% HCO$_2$H) with a 10 min gradient from 10% to 90% CH$_3$CN. The gradient was followed by a 1 min return to 10% CH$_3$CN and a 2 min flush.

Method B:

Samples were run on an HP-1100 system with an HP Zorbax SB-C$_8$ (5μ) reverse phase column (4.6×50 mm) run at 30° C. with a flow rate of 1.5 mL/min. The mobile phase used solvent A (H$_2$O/0.1% HCO$_2$H) and solvent B (CH$_3$CN/0.1% HCO$_2$H) with a 5 min gradient from 10% to 90% CH$_3$CN. The gradient was followed by a 0.5 min return to 10% CH$_3$CN and a 1.5 min flush.

EXAMPLE 1

Synthesis of 3-(2-amino-6-quinazolinyl)-1-(3-chlorophenyl)-4-methyl-2(1H)-pyridinone Step 1: 2-(4-methoxybenzyloxy)-3-bromo-4-methylpyridine To a mixture of 60% NaH in mineral oil (0.290 g, 7.27 mmol) in THF (15 mL) at RT in a resealable pressure vessel was added (4-methoxyphenyl)methanol (0.906 ml, 7.27 mmol). After 5 minutes, 3-bromo-2-chloro-4-picoline (1.00 g, 4.84 mmol) was added and the mixture was heated to 75° C. After 1 hr, water was added and the mixture was diluted with EtOAc. After washing with water and brine, the organic fraction was dried with sodium sulfate and purified by silica gel chromatography using 0-30% EtOAc:hexanes to afford 2-(4-methoxybenzyloxy)-3-bromo-4-methylpyridine as a colorless oil. M+H+=308.0.

Step 2: 6-(2-(4-methoxybenzyloxy)-4-methylpyridin-3-yl)quinazolin-2-amine

To a mixture of potassium phosphate (2.07 g, 9.73 mmol), 6-(4,4,5,5-tetramethyl-1,3,2-dioxaborolan-2-yl)quinazolin-2-amine (1.06 g, 3.89 mmol), 2-(4-methoxybenzyloxy)-3-bromo-4-methylpyridine (1.000 g, 3.24 mmol), and S-PHOS (0.162 mmol) in isopropyl alcohol (21 mL) and water (7 mL) was added palladium acetate (0.0364 g, 0.162 mmol). The mixture was stirred at 75° C. After 4 hrs, the reaction mixture was diluted with EtOAc (ca. 100 mL) and washed with water and brine. After drying with sodium sulfate, the organic fraction was stripped onto silica and purified by silica gel chromatography using 1-8% MeOH in CH$_2$Cl$_2$ w/NH$_4$OH to provide 6-(2-(4-methoxybenzyloxy)-4-methylpyridin-3-yl)quinazolin-2-amine as a tan solid. M+H+=373.1.

Step 3: 3-(2-aminoquinazolin-6-yl)-4-methylpyridin-2(1H)-one

To a solution of 6-(2-(4-methoxybenzyloxy)-4-methylpyridin-3-yl)quinazolin-2-amine (0.650 g, 1.75 mmol) in CH$_2$Cl$_2$ (1 mL) at RT was added TFA (1.00 ml, 13.0 mmol). After 10 min the solvent and excess acid was removed in vacuo. The residue was taken up in EtOAc and saturated NaHCO$_3$ was added. The resulting white precipitate was removed by filtration. The solid material, 3-(2-aminoquinazolin-6-yl)-4-methylpyridin-2(1H)-one, was dried in vacuo and used without further purification. M+H+=253.1.

Step 4: 3-(2-amino-6-quinazolinyl)-1-(3-chlorophenyl)-4-methyl-2(1H)-pyridinone

To a resealable tube was added a mixture of 3-(2-aminoquinazolin-6-yl)-4-methylpyridin-2(1H)-one (0.050 g, 0.20 mmol), potassium phosphate (0.084 g, 0.40 mmol), and copper(I) iodide (0.0075 g, 0.040 mmol) followed by Dioxane (2 mL), 1-chloro-3-iodobenzene (0.027 ml, 0.22 mmol) and N$^1$,N$^2$-dimethylethane-1,2-diamine (0.009 ml, 0.079 mmol). The resealable tube was purged with argon, sealed, and heated at 85° C. for 48 hrs. The crude mixture was filtered and concentrated in vacuo. The residue was purified by silica gel chromatography using 3-10% MeOH in CH$_2$Cl$_2$ with 1% NH$_4$OH to afford 3-(2-amino-6-quinazolinyl)-1-(3-chlorophenyl)-4-methyl-2(1H)-pyridinone as an off-white solid. M+H+=363.1.

EXAMPLE 2

Synthesis of 3-(2-aminoquinazolin-6-yl)-1-(2-cyclohexylethyl)-4-methylpyridin-2(1H)-one To a solution of 3-(2-aminoquinazolin-6-yl)-4-methylpyridin-2(1H)-one (103 mg, 408 μmol, Example 1, step 3) in DMF in a sealed tube was added sodium tert-butoxide (58.9 mg, 612 μmol). The mixture was stirred at RT for 5 min and turned from clear yellow to a suspension of yellow solids. 1-bromo-2-cyclohexylethane (76.7 μl, 490 μmol) was then added and the resulting mixture was heated to 70° C. over the weekend. Reaction was cooled to RT and was quenched with Sat'd NH$_4$Cl and extracted with DCM. Purification by prep plate TLC (10% MeOH/DCM) produced the title compound as an off white solid. M+H=363.2.

EXAMPLE 3

Synthesis of 1-(1-acetyl-3,3-dimethyl-2,3-dihydro-1H-indol-6-yl)-3-(2-amino-6-quinazolinyl)-4-methyl-2(1H)-pyridinone To a resealable tube charged with potassium phosphate (0.588 g, 2.77 mmol), 6-(4,4,5,5-tetramethyl-1,3,2-dioxaborolan-2-yl)quinazolin-2-amine (0.275 g, 1.02 mmol), 1-(1-acetyl-3,3-dimethylindolin-6-yl)-3-iodo-4-methylpyridin-2(1H)-one (0.390 g, 0.924 mmol), S-Phos (0.0227 g, 0.0554 mmol), and palladium acetate (0.0104 g, 0.0462 mmol) was added isopropyl alcohol (6.0 mL) and water (2 mL). The mixture was heated at 75° C. After 5 hrs, the mixture was diluted with EtOAc and water. The organic fraction was washed with brine and dried with sodium sulfate. After concentration in vacuo, the resulting solid was adsorbed onto silica gel and purified by silica gel chromatography using 2-10% MeOH in CH$_2$Cl$_2$ to afford 1-(1-acetyl-3,3-dimethyl-2,3-dihydro-1H-indol-6-yl)-3-(2-amino-6-quinazolinyl)-4-methyl-2(1H)-pyridinone as a white solid. M+H+=440.2.

EXAMPLE 4

Synthesis of 1-(6-iodo-3,3-dimethylindolin-1-yl)ethanone

To a suspension of 1-(6-amino-3,3-dimethylindolin-1-yl)ethanone (2.000 g, 9.791 mmol) in concentrated hydrochloric acid (20.00 ml, 548.5 mmol) at 0° was added ice (15 g) followed by a solution of sodium nitrite (0.7769 g, 11.26 mmol) in water (15 mL). After 45 min, a solution of potassium iodide (3.251 g, 19.58 mmol) in water (15 mL) was added dropwise. After 5 min, the mixture was allowed to warm to RT. After 1 hr, CH$_2$Cl$_2$ (ca. 100 mL) and water (ca. 25 mL) were added. The aqueous fraction was extracted 2× with CH$_2$Cl$_2$. The combined organic fractions were washed with saturated NaHCO$_3$ followed by 10% NaS$_2$O$_3$ and brine. After drying with Na$_2$SO$_4$, the deep red solution was concentrated in vacuo and purified by silica gel chromatography using 10-60% hexanes:EtOAc to afford 1-(6-iodo-3,3-dimethylindolin-1-yl)ethanone as an orange oil that solidified upon standing. M+H+=316.0.

The following compounds, Examples 5-61 were made using a procedure similar to that described in Examples 1 and 2.

| Ex. No. | Name | M + H$^+$ | HTRF Fret enzyme assay data (uM) | UT7 Proliferation cell assay data (uM) |
|---|---|---|---|---|
| 5 | 1-(4-(1H-pyrrol-1-yl)phenyl)-3-(2-aminoquinazolin-6-yl)-4-methylpyridin-2(1H)-one | 394.2 | 0.002252 | 0.004825 |
| 6 | 3-(2-aminoquinazolin-6-yl)-1-(3-fluoro-4-methylphenyl)-4-methylpyridin-2(1H)-one | 361.3 | 0.040101 | 0.012119 |
| 7 | 3-(2-aminoquinazolin-6-yl)-4-methyl-1-(4-(oxazol-2-yl)phenyl)pyridin-2(1H)-one | 396.1 | 0.021577 | 0.0155 |
| 8 | 3-(2-aminoquinazolin-6-yl)-1-(3,5-dimethylphenyl)-4-methylpyridin-2(1H)-one | 357.1 | 0.016082 | 0.050062 |
| 9 | 3-(3-(2-aminoquinazolin-6-yl)-4-methyl-2-oxopyridin-1(2H)-yl)benzonitrile | 354.1 | 0.088827 | 0.1067 |
| 10 | 3-(2-aminoquinazolin-6-yl)-4-methyl-1-(2-(trifluoromethyl)-1H-benzo[d]imidazol-5-yl)pyridin-2(1H)-one | 437.7 | 0.034757 | 0.189 |
| 11 | 3-(2-aminoquinazolin-6-yl)-1-(3-methoxy-5-(trifluoromethyl)phenyl)-4-methylpyridin-2(1H)-one | 427.1 | 0.011111 | 0.0588 |
| 12 | 3-(2-amino-6-quinazolinyl)-1-(4-(1,1-dimethylethyl)phenyl)-4-methyl-2(1H)-pyridinone | 385.1 | 0.002063 | 0.016494 |
| 13 | 3-(2-amino-6-quinazolinyl)-1-(3,4-dimethylphenyl)-4-methyl-2(1H)-pyridinone | 357.2 | 0.003667 | 0.0054 |
| 14 | 3-(2-amino-6-quinazolinyl)-4-methyl-1-(3-((trifluoromethyl)oxy)phenyl)-2(1H)-pyridinone | 413 | 0.004036 | 0.0162 |
| 15 | 3-(2-amino-6-quinazolinyl)-1-(3,3-dimethyl-2,3-dihydro-1H-indol-6-yl)-4-methyl-2(1H)-pyridinone | 398.2 | 0.0047 | 0.019393 |
| 16 | 3-(2-amino-6-quinazolinyl)-4-methyl-1-(6-quinolinyl)-2(1H)-pyridinone | 380.2 | 0.005289 | 0.05682 |
| 17 | 3-(2-amino-6-quinazolinyl)-1-(2,3-dihydro-1-benzofuran-5-yl)-4-methyl-2(1H)-pyridinone | 371.2 | 0.007576 | 0.015055 |
| 18 | 3-(2-amino-6-quinazolinyl)-4-methyl-1-(1H-indol-5-yl)-2(1H)-pyridinone | 368.2 | 0.008651 | 0.028834 |
| 19 | 1-(1-acetyl-3,3-dimethyl-2,3-dihydro-1H-indol-6-yl)-3-(2-amino-6-quinazolinyl)-4-methyl-2(1H)-pyridinone | 440.2 | 0.00975 | 0.226196 |
| 20 | 3-(2-amino-6-quinazolinyl)-4-methyl-1-(3-(trifluoromethyl)phenyl)-2(1H)-pyridinone | 397.2 | 0.014062 | 0.027911 |

-continued

| Ex. No. | Name | M + H⁺ | HTRF Fret enzyme assay data (uM) | UT7 Proliferation cell assay data (uM) |
|---|---|---|---|---|
| 21 | 3-(2-amino-6-quinazolinyl)-4-methyl-1-(3-(trifluoromethyl)phenyl)-2(1H)-pyridinone | 387.2 | 0.015465 | 0.020002 |
| 22 | 3-(2-amino-6-quinazolinyl)-4-methyl-1-(3-(methyloxy)phenyl)-2(1H)-pyridinone | 359.2 | 0.065284 | 0.027697 |
| 21 | 3-(2-amino-6-quinazolinyl)-4-methyl-1-phenyl-2(1H)-pyridinone | 329.1 | 0.205043 | |
| 24 | 3-(2-aminoquinazolin-6-yl)-1-benzyl-4-methylpyridin-2(1H)-one | 343.1 | 0.006 | 0.013 |
| 25 | 3-(2-aminoquinazolin-6-yl)-1-isopentyl-4-methylpyridin-2(1H)-one | 323.2 | 0.018 | 0.084 |
| 26 | 3-(2-amino-6-quinazolinyl)-1-(1'H-1,5'-biindol-5-yl)-4-methyl-2(1H)-pyridinone | 483.2 | 0.002 | 0.011 |
| 27 | 3-(2-aminoquinazolin-6-yl)-1-(4-isopropylphenyl)-4-methylpyridin-2(1H)-one | | 0.002 | 0.005 |
| 28 | 1-(4-acetylphenyl)-3-(2-aminoquinazolin-6-yl)-4-methylpyridin-2(1H)-one | | 0.02 | 0.031 |
| 29 | ethyl 4-(3-(2-aminoquinazolin-6-yl)-4-methyl-2-oxopyridin-1(2H)-yl)benzoate | | 0.017 | 0.066 |
| 30 | 3-(2-aminoquinazolin-6-yl)-4-methyl-1-(4-(trifluoromethyl)phenyl)pyridin-2(1H)-one | | 0.008 | 0.018 |
| 31 | 3-(2-aminoquinazolin-6-yl)-1-(4-methoxyphenyl)-4-methylpyridin-2(1H)-one | | 0.017 | 0.018 |
| 32 | 3-(2-aminoquinazolin-6-yl)-1-(4-chlorophenyl)-4-methylpyridin-2(1H)-one | | 0.02 | 0.014 |
| 33 | 3-(2-aminoquinazolin-6-yl)-1-(4-fluorophenyl)-4-methylpyridin-2(1H)-one | | 0.063 | 0.107 |
| 34 | 3-(2-aminoquinazolin-6-yl)-4-methyl-1-(4-morpholinophenyl)pyridin-2(1H)-one | | 0.013 | 0.072 |
| 35 | 3-(2-aminoquinazolin-6-yl)-4-methyl-1-(4-(morpholinomethyl)phenyl)pyridin-2(1H)-one | | 0.031 | 0.2 |
| 36 | tert-butyl 4-(4-(3-(2-aminoquinazolin-6-yl)-4-methyl-2-oxopyridin-1(2H)-yl)phenyl)piperazine-1-carboxylate | | 1.37 | |
| 37 | ethyl 2-(4-(3-(2-aminoquinazolin-6-yl)-4-methyl-2-oxopyridin-1(2H)-yl)phenylamino)acetate | | 0.181 | |
| 38 | 1-(4-(1H-pyrazol-1-yl)phenyl)-3-(2-aminoquinazolin-6-yl)-4-methylpyridin-2(1H)-one | | 0.01 | 0.018 |
| 39 | 3-(2-aminoquinazolin-6-yl)-1-(3,4-difluorophenyl)-4-methylpyridin-2(1H)-one | | 0.048 | 0.063 |
| 40 | 3-(2-aminoquinazolin-6-yl)-1-(3,4-dichlorophenyl)-4-methylpyridin-2(1H)-one | | 0.02 | 0.018 |
| 41 | 3-(2-aminoquinazolin-6-yl)-1-(3-chloro-4-methylphenyl)-4-methylpyridin-2(1H)-one | | 0.008213 | 0.012 |
| 42 | 3-(2-aminoquinazolin-6-yl)-1-(4-fluoro-3-methylphenyl)-4-methylpyridin-2(1H)-one | | 0.013991 | 0.018 |

-continued

| Ex. No. | Name | M + H⁺ | HTRF Fret enzyme assay data (uM) | UT7 Proliferation cell assay data (uM) |
|---|---|---|---|---|
| 43 | 3-(2-aminoquinazolin-6-yl)-1-(4-fluoro-3-(trifluoromethyl)phenyl)-4-methylpyridin-2(1H)-one | | 0.021216 | 0.041 |
| 44 | 3-(2-aminoquinazolin-6-yl)-1-(4-chloro-3-fluorophenyl)-4-methylpyridin-2(1H)-one | | 0.059738 | 0.022 |
| 45 | 3-(2-aminoquinazolin-6-yl)-1-(3-chloro-4-fluorophenyl)-4-methylpyridin-2(1H)-one | | 0.098881 | 0.04 |
| 46 | 3-(2-aminoquinazolin-6-yl)-1-(3,5-dichlorophenyl)-4-methylpyridin-2(1H)-one | | 0.044011 | 0.035 |
| 47 | 3-(2-aminoquinazolin-6-yl)-1-(cyclohexylmethyl)-4-methylpyridin-2(1H)-one | | 0.131777 | |
| 48 | 3-(2-aminoquinazolin-6-yl)-1-(cyclobutylmethyl)-4-methylpyridin-2(1H)-one | | 1.410674 | |
| 49 | 3-(2-aminoquinazolin-6-yl)-1-isobutyl-4-methylpyridin-2(1H)-one | | 2.253343 | |
| 50 | 3-(2-aminoquinazolin-6-yl)-4-methyl-1-propylpyridin-2(1H)-one | | 0.314998 | |
| 51 | methyl 2-(3-(2-aminoquinazolin-6-yl)-4-methyl-2-oxopyridin-1(2H)-yl)acetate | | 1.188901 | |
| 52 | 3-(2-aminoquinazolin-6-yl)-1-(2-cyclopentylethyl)-4-methylpyridin-2(1H)-one | | 0.000818 | 0.024 |
| 53 | 3-(2-aminoquinazolin-6-yl)-1-butyl-4-methylpyridin-2(1H)-one | | 0.11781 | |
| 54 | 3-(2-aminoquinazolin-6-yl)-4-methyl-1-(3-methylbut-2-enyl)pyridin-2(1H)-one | | 0.023874 | 0.012 |
| 55 | 3-(2-aminoquinazolin-6-yl)-1-(2-(dimethylamino)ethyl)-4-methylpyridin-2(1H)-one | | 1.584529 | |
| 56 | 3-(2-aminoquinazolin-6-yl)-1-(2-methoxyethyl)-4-methylpyridin-2(1H)-one | | 2.227117 | |
| 57 | 3-(2-aminoquinazolin-6-yl)-1-(3,3-dimethylbutyl)-4-methylpyridin-2(1H)-one | | 0.016311 | 0.043 |
| 58 | 3-(2-aminoquinazolin-6-yl)-4-methyl-1-(3-methylpentyl)pyridin-2(1H)-one | | 0.002508 | 0.009 |
| 59 | 3-(2-aminoquinazolin-6-yl)-1-(2-cyclopropylethyl)-4-methylpyridin-2(1H)-one | | 0.078886 | 0.028 |
| 60 | 1-(2-(1H-pyrazol-1-yl)ethyl)-3-(2-aminoquinazolin-6-yl)-4-methylpyridin-2(1H)-one | | 0.176364 | |
| 61 | 3-(2-aminoquinazolin-6-yl)-4-methyl-1-(4-methylpentyl)pyridin-2(1H)-one | | 0.001119 | 0.004 |

The following compounds in Tables 1 and 2 are additional representative examples of compounds of Formula I, as provided by the present invention.

TABLE 1

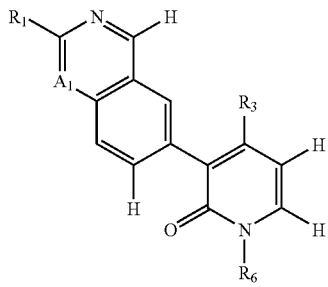

| Ex. No. | R$^1$ | A$^1$ | R$^3$ | R$^6$ |
|---|---|---|---|---|
| 62 | cyclohexyl-HN—(CH$_2$)$_2$—N— | N | Methyl | N-acetylindoline |
| 63 | piperidine-(CH$_2$)$_2$—N— | N | chloro | dimethylindoline |
| 64 | NH$_2$ | N | Methyl | pyrimidine |
| 65 | H | N | Methyl or chloro | 2-CH$_3$-phenyl |
| 66 | NH$_2$ | N | Methyl or chloro | 4-CF$_3$-phenyl |
| 67 | 1-piperidinyl | N | Methyl or chloro | 3-CF$_3$-phenyl |
| 68 | cyclohexyl-N— | N | Methyl or chloro | 6-CH$_3$-phenyl |
| 69 | morpholine-(CH$_2$)$_2$—N— | CH | Methyl or chloro | 2-OCH$_3$-phenyl |
| 70 | (CH$_3$)$_2$N—(CH$_2$)$_2$—N— | CH | Methyl or chloro | 4-OCH$_3$-phenyl |
| 71 | (C$_2$H$_5$)$_2$N—(CH$_2$)$_2$—N— | CH | Methyl or chloro | pyridine |
| 72 | 3-OH-1-pyrrolidinyl | CH | Methyl or chloro | indole |
| 73 | 3-amido-1-pyrrolidinyl | CH | Methyl or chloro | indoline |
| 74 | 4-amido-1-piperidinyl | CH | Methyl or chloro | benzofuran |
| 75 | 3-amido-1-piperidinyl | CH | Methyl or chloro | 2-F-phenyl |
| 76 | 4N—CH$_3$-1-piperizinyl | CH | Methyl or chloro | 4-F-phenyl |
| 77 | H | N | Methyl or chloro | Dihydrobenzofuran |
| 78 | NH$_2$ | N | Methyl or cyclopropyl | cyclohexyl-(CH$_2$)$_2$— |
| 79 | 4-CH$_3$-phenyl | N | Methyl or cyclopropyl | cyclopropyl-(CH$_2$)$_2$— |
| 80 | H | N | Methyl or cyclopropyl | 2-CH$_3$-phenyl |
| 81 | NH$_2$ | N | Methyl or cyclopropyl | 4-CF$_3$-phenyl |
| 82 | H | CH | Methyl or cyclopropyl | 3-CF$_3$-phenyl |
| 83 | NH$_2$ | CH | Methyl or cyclopropyl | 6-CH$_3$-phenyl |
| 84 | 3-thiophene | CH | Methyl or cyclopropyl | 2-OCH$_3$-phenyl |
| 85 | H | CH | Methyl or cyclopropyl | 4-OCH$_3$-phenyl |
| 86 | NH$_2$ | CH | Methyl or cyclopropyl | pyridine |
| 87 | 1-piperazinyl | CH | Methyl or cyclopropyl | indole |
| 88 | 1-piperidinyl | CH | Methyl or cyclopropyl | indoline |
| 89 | cyclohexyl-N— | CH | Methyl or cyclopropyl | benzofuran |
| 90 | morpholine-(CH$_2$)$_2$—N— | N | Methyl or cyclopropyl | 2-F-phenyl |
| 91 | (CH$_3$)$_2$N—(CH$_2$)$_2$—N— | N | Methyl or cyclopropyl | 4-F-phenyl |

TABLE 1-continued

[Structure diagram of compound with R1, N, H, A1, R3, H, O, N, R6 substituents]

| Ex. No. | R¹ | A¹ | R³ | R⁶ |
|---|---|---|---|---|
| 92 | (C₂H₅)₂N—(CH₂)₂—N— | N | Methyl or cyclopropyl | dihydrobenzofuran |
| 93 | H | N | Methyl or cyclopropyl | 2-CH₃-phenyl |
| 94 | NH₂ | N | Methyl or cyclopropyl | 4-CF₃-phenyl |
| 95 | 3-amido-1-piperidinyl | N | Methyl or cyclopropyl | 3-CF₃-phenyl |
| 96 | 4-amido-1-piperidinyl | N | Methyl or cyclopropyl | 6-CH₃-phenyl |
| 97 | H | N | Methyl or cyclopropyl | 2-OCH₃-phenyl |
| 98 | NH₂ | N | Methyl or cyclopropyl | 4-OCH₃-phenyl |
| 99 | H | N | Methyl or cyclopropyl | pyridine |
| 100 | NH₂ | N | Methyl or cyclopropyl | indole |
| 101 | H | N | Methyl or cyclopropyl | indoline |
| 102 | NH₂ | CH | Methyl or cyclopropyl | benzofuran |
| 103 | H | CH | Methyl or cyclopropyl | 2-F-phenyl |
| 104 | NH₂ | CH | Methyl or cyclopropyl | 4-F-phenyl |
| 105 | H | CH | Methyl or cyclopropyl | dihydrobenzofuran |
| 106 | NH₂ | CH | Methyl or cyclopropyl | cyclohexyl-(CH₂)₂— |
| 107 | 1-morpholinyl | CH | Methyl or cyclopropyl | cyclopropyl-(CH₂)₂— |
| 108 | H | CH | Methyl or cyclopropyl | 2-CH₃-phenyl |
| 109 | NH₂ | CH | Methyl or cyclopropyl | 4-CF₃-phenyl |
| 110 | H | CH | Methyl or cyclopropyl | 3-CF₃-phenyl |
| 111 | NH₂ | CH | Methyl or cyclopropyl | 6-CH₃-phenyl |
| 112 | H | CH | Methyl or cyclopropyl | 2-OCH₃-phenyl |
| 113 | NH₂ | CH | Methyl or cyclopropyl | 4-OCH₃-phenyl |
| 114 | H | CH | m-C(O)NH— | pyridine |
| 115 | NH₂ | N | Methyl or cyclopropyl | indole |
| 116 | H | N | Methyl or cyclopropyl | indoline |
| 117 | NH₂ | N | Methyl or cyclopropyl | benzofuran |
| 118 | H | N | Methyl or cyclopropyl | 2-F-phenyl |
| 119 | NH₂ | N | Methyl or cyclopropyl | 4-F-phenyl |
| 120 | H | N | Methyl or cyclopropyl | dihydrobenzofuran |
| 121 | NH₂ | N | Methyl or cyclopropyl | cyclohexyl-(CH₂)₂— |
| 122 | NH₂ | N | Methyl or cyclopropyl | cyclopropyl-(CH₂)₂— |

TABLE 1-continued

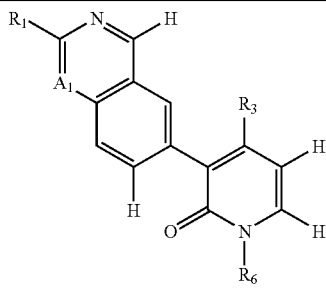

| Ex. No. | R¹ | A¹ | R³ | R⁶ |
|---|---|---|---|---|
| 123 | H | N | Methyl or cyclopropyl | 2-thiophene |
| 124 | $NH_2$ | N | Methyl or cyclopropyl | 3-thiophene |
| 125 | H | N | Methyl or cyclopropyl | 2-pyridine |
| 126 | $NH_2$ | N | Methyl or cyclopropyl | 1-morpholinyl |
| 127 | $(CH_3)NH-(CH_2)_2-N-$ | CH | Methyl or cyclopropyl | 1-piperazinyl |
| 128 | $(C_2H_5)NH-(CH_2)_2-N-$ | N | Methyl or cyclopropyl | 1-piperidinyl |

TABLE 2

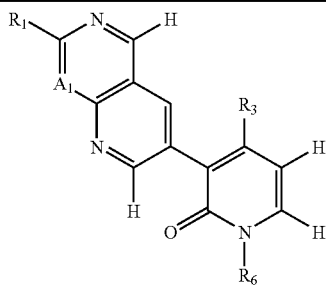

| Ex. No. | R¹ | A¹ | R³ | R⁶ |
|---|---|---|---|---|
| 129 | H | N | Methyl or chloro | 2-$CH_3$-phenyl |
| 130 | $NH_2$ | N | Methyl or chloro | 4-$CF_3$-phenyl |
| 131 | 1-piperidinyl | N | Methyl or chloro | 3-$CF_3$-phenyl |
| 132 | cyclohexyl-N— | N | Methyl or chloro | 6-$CH_3$-phenyl |
| 133 | morpholine-$(CH_2)_2$—N— | CH | Methyl or chloro | 2-$OCH_3$-phenyl |
| 134 | $(CH_3)_2N-(CH_2)_2-N-$ | CH | Methyl or chloro | 4-$OCH_3$-phenyl |
| 135 | $(C_2H_5)_2N-(CH_2)_2-N-$ | CH | Methyl or chloro | pyridine |
| 136 | 3-OH-1-pyrrolidinyl | CH | Methyl or chloro | indole |
| 137 | 3-amido-1-pyrrolidinyl | CH | Methyl or chloro | indoline |
| 138 | 4-amido-1-piperidinyl | CH | Methyl or chloro | benzofuran |
| 139 | 3-amido-1-piperidinyl | CH | Methyl or chloro | 2-F-phenyl |
| 140 | 4N—$CH_3$-1-piperizinyl | CH | Methyl or chloro | 4-F-phenyl |
| 141 | H | N | Methyl or chloro | Dihydrobenzofuran |
| 142 | $NH_2$ | N | Methyl or cyclopropyl | cyclohexyl-$(CH_2)_2$— |
| 143 | 4-$CH_3$-phenyl | N | Methyl or cyclopropyl | cyclopropyl-$(CH_2)_2$— |
| 144 | H | N | Methyl or cyclopropyl | 2-$CH_3$-phenyl |
| 145 | $NH_2$ | N | Methyl or cyclopropyl | 4-$CF_3$-phenyl |
| 146 | H | CH | Methyl or cyclopropyl | 3-$CF_3$-phenyl |
| 147 | $NH_2$ | CH | Methyl or cyclopropyl | 6-$CH_3$-phenyl |
| 148 | 3-thiophene | CH | Methyl or cyclopropyl | 2-$OCH_3$-phenyl |

TABLE 2-continued

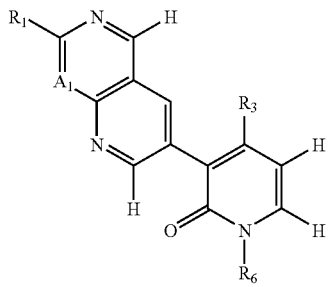

| Ex. No. | R¹ | A¹ | R³ | R⁶ |
|---|---|---|---|---|
| 149 | H | CH | Methyl or cyclopropyl | 4-OCH₃-phenyl |
| 150 | NH₂ | CH | Methyl or cyclopropyl | pyridine |
| 151 | 1-piperazinyl | CH | Methyl or cyclopropyl | indole |
| 152 | 1-piperidinyl | CH | Methyl or cyclopropyl | indoline |
| 153 | cyclohexyl-N— | CH | Methyl or cyclopropyl | benzofuran |
| 154 | morpholine-(CH₂)₂—N— | N | Methyl or cyclopropyl | 2-F-phenyl |
| 155 | (CH₃)₂N—(CH₂)₂—N— | N | Methyl or cyclopropyl | 4-F-phenyl |
| 156 | (C₂H₅)₂N—(CH₂)₂—N— | N | Methyl or cyclopropyl | dihydrobenzofuran |
| 157 | H | N | Methyl or cyclopropyl | 2-CH₃-phenyl |
| 158 | NH₂ | N | Methyl or cyclopropyl | 4-CF₃-phenyl |
| 159 | 3-amido-1-piperidinyl | N | Methyl or cyclopropyl | 3-CF₃-phenyl |
| 160 | 4-amido-1-piperidinyl | N | Methyl or cyclopropyl | 6-CH₃-phenyl |
| 161 | H | N | Methyl or cyclopropyl | 2-OCH₃-phenyl |
| 162 | NH₂ | N | Methyl or cyclopropyl | 4-OCH₃-phenyl |
| 163 | H | N | Methyl or cyclopropyl | pyridine |
| 164 | NH₂ | N | Methyl or cyclopropyl | indole |
| 165 | H | N | Methyl or cyclopropyl | indoline |
| 166 | NH₂ | CH | Methyl or cyclopropyl | benzofuran |
| 167 | H | CH | Methyl or cyclopropyl | 2-F-phenyl |
| 168 | NH₂ | CH | Methyl or cyclopropyl | 4-F-phenyl |
| 169 | H | CH | Methyl or cyclopropyl | dihydrobenzofuran |
| 170 | NH₂ | CH | Methyl or cyclopropyl | cyclohexyl-(CH₂)₂— |
| 171 | 1-morpholinyl | CH | Methyl or cyclopropyl | cyclopropyl-(CH₂)₂— |
| 172 | H | CH | Methyl or cyclopropyl | 2-CH₃-phenyl |
| 173 | NH₂ | CH | Methyl or cyclopropyl | 4-CF₃-phenyl |
| 174 | H | CH | Methyl or cyclopropyl | 3-CF₃-phenyl |
| 175 | NH₂ | CH | Methyl or cyclopropyl | 6-CH₃-phenyl |
| 176 | H | CH | Methyl or cyclopropyl | 2-OCH₃-phenyl |

TABLE 2-continued

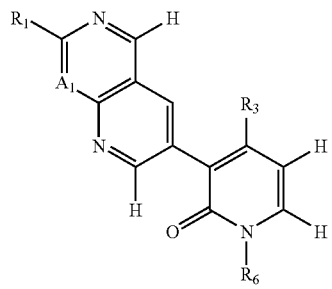

| Ex. No. | R¹ | A¹ | R³ | R⁶ |
|---|---|---|---|---|
| 177 | NH₂ | CH | Methyl or cyclopropyl | 4-OCH₃-phenyl |
| 178 | H | CH | m-C(O)NH— | pyridine |
| 179 | NH₂ | N | Methyl or cyclopropyl | indole |
| 180 | H | N | Methyl or cyclopropyl | indoline |
| 181 | NH₂ | N | Methyl or cyclopropyl | benzofuran |
| 182 | H | N | Methyl or cyclopropyl | 2-F-phenyl |
| 183 | NH₂ | N | Methyl or cyclopropyl | 4-F-phenyl |
| 184 | H | N | Methyl or cyclopropyl | dihydrobenzofuran |
| 185 | NH₂ | N | Methyl or cyclopropyl | cyclohexyl-(CH₂)₂— |
| 186 | NH₂ | N | Methyl or cyclopropyl | cyclopropyl-(CH₂)₂— |
| 187 | H | N | Methyl or cyclopropyl | 2-thiophene |
| 188 | NH₂ | N | Methyl or cyclopropyl | 3-thiophene |
| 189 | H | N | Methyl or cyclopropyl | 2-pyridine |
| 190 | NH₂ | N | Methyl or cyclopropyl | 1-morpholinyl |
| 191 | (CH₃)NH—(CH₂)₂—N— | CH | Methyl or cyclopropyl | 1-piperazinyl |
| 192 | (C₂H₅)NH—(CH₂)₂—N— | N | Methyl or cyclopropyl | 1-piperidinyl |

The following examples represent methods by which various of the building block starting materials or intermediates described herein may be made.

EXAMPLE 193

Synthesis of 3-bromo-4-methylpyridin-2(1H)-one

To a resealable pressure vessel charged with 3-bromo-2-chloro-4-picoline (1.200 g, 5.81 mmol) was added formic acid (13.1 ml, 348 mmol) and water (4.00 ml, 222 mmol). The tube was sealed and the solution heated to 120° C. After 72 hrs, the solution was cooled to RT and concentrated in vacuo. The residue was purified by reverse phase chromatography (neutral) to afford 3-bromo-4-methylpyridin-2(1H)-one as a white solid. M+H+=188.0.

EXAMPLE 194

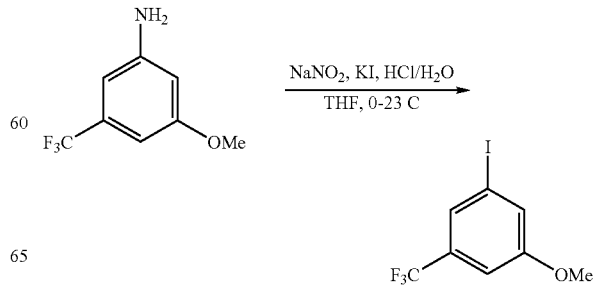

Synthesis of
1-iodo-3-methoxy-5-(trifluoromethyl)benzene

A solution of conc. HCl in H20 (1:1 v/v, 1.1 ml) was added to a solution of 3-methoxy-5-(trifluoromethyl)benzenamine (250 mg, 1308 μmol) in THF (2 ml). The mixture was stirred at RT for 1 hr and then cooled to 0 C. A chilled solution of sodium nitrite (208 mg, 3008 μmol) in $H_2O$ (2 ml) was added slowly. Additional $H_2O$ (0.8 ml) was added. A solution of potassium iodide (369 mg, 2223 μmol) in H20 (0.415 ml) was added dropwise. Additional $H_2O$ (0.62 ml) and THF (3.9 ml) was added and the reaction mixture was then gradually warmed to room temperature and stirred overnight. Analysis by LCMS indicated the reaction was complete. Saturated aqueous $Na_2CO_3$ was added, the volatiles were removed by rotovap, and the mixture was partitioned with DCM. The aqueous layer was extracted with DCM (2×), the organic layers were combined and washed with brine and dried over $Na_2SO_4$. Purification by Biotage was performed using 100% Hexanes to give a clear oil (208 mg, 53% yield).

EXAMPLE 195

Synthesis of 3-iodo-4-methyl-1-(3-(trifluoromethoxy)phenyl)pyridin-2(1H)-one

A resealable pressure vessel was charged with copper(I) iodide (0.081 g, 0.425 mmol), 1-iodo-3-(trifluoromethoxy)benzene (0.434 ml, 2.77 mmol) and 3-bromo-4-methylpyridin-2(1H)-one (0.400 g, 2.13 mmol). To the mixture was added dioxane (3 mL) followed by $N^1,N^2$-dimethylethane-1,2-diamine (0.092 ml, 0.851 mmol). The vessel was purged with Argon, sealed, and heated to 110° C. for 24 hrs. The mixture was cooled to RT, diluted with EtOAc and washed with water and brine. The organic fraction was adsorbed onto silica gel and purified by silica gel chromatography using 15-80% Hexanes: EtOAc to afford 3-iodo-4-methyl-1-(3-(trifluoromethoxy)phenyl)pyridin-2(1H)-one as an off-white solid. M+H+=396.0.

While the examples described above provide processes for synthesizing compounds of Formula I, other methods may be utilized to prepare such compounds. Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

All process steps described herein can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H+ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example, under argon or nitrogen.

Salts may be present in all starting compounds and transients, if these contain salt-forming groups. Salts may also be present during the reaction of such compounds, provided the reaction is not thereby disturbed.

The solvents from which those can be selected which are suitable for the reaction in question include, for example, water, esters, typically lower alkyl-lower alkanoates, e.g. EtOAc, ethers, typically aliphatic ethers, e.g. $Et_2O$, or cyclic ethers, e.g. THF, liquid aromatic hydrocarbons, typically benzene or toluene, alcohols, typically MeOH, EtOH, IPA or 1-propanol, nitriles, typically AcCN, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. HOAc, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient species and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of formula I or II, including their salts, are also obtainable in the form of hydrates, or their crystals can include for example the solvent used for crystallization (present as solvates).

New starting materials and/or intermediates, as well as processes for the preparation thereof, are likewise the subject of this invention. In one embodiment, such starting materials are used and reaction conditions so selected as to enable the preferred compounds to be obtained. Starting materials of the invention, are known, are commercially available, or can be synthesized in analogy to or according to methods that are known in the art. In the preparation of starting materials, existing functional groups which do not participate in the reaction should, if necessary, be protected. Preferred protecting groups, their introduction and their removal are described above or in the examples. All remaining starting materials are known, capable of being prepared according to known processes, or commercially obtainable; in particular, they can be prepared using processes as described in the examples.

The examples above serve to illustrate various embodiments of the invention. The tables also contain the method by which these examples were prepared, with respect to the various schemes and examples presented above. The schematic illustrations, detailed description of the methods and preparation of compounds of Formulas I or II, and compounds described above fall within, and serve to exemplify, the scope of compounds contemplated in the invention. These detailed method descriptions are presented for illustrative purposes only and are not intended as a restriction on the scope of the present invention.

Biological Assays

The following assays can be employed to determine the degree of activity of a compound as a c-kit protein kinase modulator. Compounds described herein have been tested in one or more of these assays, and have shown activity. Representative compounds of the invention were tested and found to exhibit IC50 values of at least <10 μM in any one of the described assays, thereby demonstrating and confirming the utility of the compounds of the invention as c-kit kinase inhibitors and in the prophylaxis and treatment of c-kit kinase activity-related disorders.

C-kit-homogeneous Time Resolved Fluorescent (HTRF) Kinase Assay:

The purpose of this assay is to measure the inhibition of c-kit enzyme activity (autophosphorylation and phosphorylation of substrate) by small molecule test compounds. The c-kit HTRF assay begins with c-kit-catalyzed phosphorylation of biotinylated peptide Her-2 (N-GGMEDIYFEFMG-GKKK-C) in the presence of ATP. The c-kit enzyme reaction is comprised of 1 μL of compound in 100% DMSO, 15 μL of 2× substrate mix (50 μM ATP and 2 μM biotinylated Her-2) and 15 μL of 2× c-kit (6.25 μM) (catalytic domain, N-terminal GST tagged, unphosphorylated) in 4 mM DTT all diluted in enzyme buffer (25 mM HEPES pH 7.5, 12.5 mM NaCl, 50 mM MgCl, 0.05% BSA). The reaction incubates for 90 min at RT. 160 Microliters of detection mixture containing 0.47 μg/mL steptavidin allophycocyanin and 29.7 pM europylated anti-phosphotyrosine Ab (PT66, Perkin Elmer) in HTRF buffer (100 mM Hepes pH 7.5, 100 mM NaCl, 0.1% BSA, 0.05% Tween 20) is then added to stop the reaction, by diluting out the enzyme as well as to enable quantitation of phosphorylated Her-2. After 3 h at RT, the detection reaction is read in a Packard Discovery™ (model BD1000) plate reader. The wells are excited with coherent 320 nM light and the ratio of delayed (50 ms post excitation) emissions at 620 nM (native europium fluorescence) and 665 nm (europium fluorescence transferred to allophycocyanin—an index of substrate phosphorylation) is determined. The proportion of substrate phosphorylated in the kinase reaction in the presence of compound compared with that phosphorylated in the presence of DMSO vehicle alone (HI control) is calculated using the formula: % control (POC)=(cpd−average LO)/(average HI−average LO)*100. Data (consisting of POC and inhibitor concentration in μM) is fitted to a 4-parameter equation (y=A+((B−A)/(1+((x/C)^D))), where A is the minimum y (POC) value, B is the maximum y (POC), C is the x (compound concentration) at the point of inflection and D is the slope factor) using a Levenburg-Marquardt non-linear regression algorithm.

Of the compounds tested, exemplary compounds 1-2 and 5-35, 37-47, 50, 52-54 and 57-61 exhibited an average $IC_{50}$ value of 1.0 uM or less in a human HTRF assay, for the inhibition of the c-kit kinase enzyme. The specific activities are provided herein.

MO7e Phosphorylated-c-kit (Tyr721) Electrochemiluminescent Immunoassay:

The purpose of this assay is to test the potency of small molecule compounds on SCF-stimulated c-kit receptor phosphorylation of tyrosine 721 (Tyr721) in MO7e cells. Activation of c-kit upon binding with it's ligand, stem cell factor (SCF), leads to dimerization/oligomerization and autophosphorylation. Activation of c-kit results in the recruitment and tyrosine phosphorylation of downstream SH2-containing signaling components—such as the p85 subunit of PI3 kinase (Sattler, M. et al. (1997) *J. Biol. Chem.* 272, 10248-10253). C-kit phosphorylated at Tyr721 binds to the p85 subunit of PI3 kinase (Blume-Jensen, P et al. (2000) *Nature Genet.* 24, 157-162). MO7e cells are a human megakaryoblastic factor dependent leukemia cell line (these cells have been confirmed to carry wild type c-kit receptor). Cells are maintained in growth media (IMDM, 10% HI-FBS, 1×PGS, 5 ng/mL GM-CSF). To measure SCF-induced c-kit phosphorylation, cells are washed and resuspended to 3.3E5 c/mL in assay media (RPMI 1640/4% HI-FBS, 1×PGS) and plated at 30 uL/well for 10000 c/well. Small molecule compounds are diluted in 100% DMSO. Cells are pre-incubated with 0.5-2 μL compound for 1 h at RT. 10 Microliters of 4×SCF (100 ng/mL) in RT assay media is then added. After 30 min incubation at RT, the cells are lysed with the addition of 20 μL of ice cold 3× lysis buffer (20 mM Tris-Cl, 1 mM EDTA, 150 mM NaCl, 1% NP-40, 2 mM NaF, 20 mM □-glycerophosphate, 1 mM $Na_3VO_4$ and 1 Complete Proteinase inhibitor tablet/50 mL 1× lysis buffer (Roche Cat #1697498, in stock room)). 25 Microliters of lysate is transferred to blocked MSD plates (blocked with 5% BSA in Tris-buffered saline, 0.01% Tween (TBS-T) for 1 h with shaking, then washed 3× with TBS-T) coated with anti-c-kit antibody (Labvision MS-289). After the plates are incubated with shaking for 1 h at RT, 25 μL of 10 nM ruthenylated detection antibody (Zymed 34-9400) is added and the plate is incubated again with shaking for 1 h at RT. The plates are then washed 3× with TBS-T, 150 μL of MSD Read Buffer T is added, and the electrochemiluminescence (ECL) reaction is read on the Sector Imager™ 6000. A low voltage is applied to the ruthenylated phos-c-kit (Tyr721) immune complexes, which in the presence of TPA (the active component in the ECL reaction buffer, Read Buffer T), results in a cyclical redox reaction generating light at 620 nm. The amount of phosphorylated c-kit (Tyr721) in the presence of compounds compared with that in the presence of vehicle alone (HI control) is calculated using the formula: % control (POC)= (cpd−average LO)/(average HI−average LO)*100. Data (consisting of POC and inhibitor concentration in μM) is fitted to a 4-parameter equation (y=A+((B−A)/(1+((x/C)^D))), where A is the minimum y (POC) value, B is the maximum y (POC), C is the x (cpd concentration) at the point of inflection and D is the slope factor) using a Levenburg-Marquardt non-linear regression algorithm.

SCF and GM-CSF Stimulated UT7 Proliferation/Survival Assay:

The purpose of this assay is to test the general anti-proliferative/cytotoxic effect of small molecule compounds on SCF or GM-CSF-stimulated UT-7 cells. Preventing SCF stimulated proliferation/survival is consistent with an on-mechanism effect whereas inhibition of GM-CSF driven proliferation/survival is indicative of off-target effects. UT-7 is a factor dependent human megakaryoblastic leukemia cell line that can be grown in either IL-3, GM-CSF, EPO or SCF (these cells have been confirmed to carry wild type c-kit receptor). Cells are maintained in growth media (IMDM, 10% HI-FBS, 1×PGS, 1 ng/mL GM-CSF). To measure SCF or GM-CSF-induced proliferation, cells are washed and re-suspended to 5e4 c/mL in assay media (RPMI 1640/4% HI-FBS, 1×PGS) and plated at 50 uL/well for 2500 c/well. Small molecule compounds are first diluted in 100% DMSO, then diluted 1:4 in RT assay media. 5 Microliters of 11×SCF (55 ng/mL) or 11×GM-CSF (11 ng/mL) in assay media plus 1 μL of diluted drug are added to the cell plates. The treated cells are incubated in a 37° C. humidified incubator with 5% $CO_2$ for 3 days. The amount of ATP is then measured as a surrogate marker for cell viability. This is accomplished by adding 50 μL of Perkin Elmer ATP 1 step reagent (as per instructed in the reagent manual, Cat. No. 6016739), incubating at RT for 15 min and reading the luminescence with a Perkin Elmer Topcount NXT™HTS (model c384) plate reader. The amount of SCF or GM-CSF stimulated viable cells in the presence of compound compared with in the presence of vehicle alone (HI control) is calculated using the formula: % control (POC) =(cpd−average LO)/(average HI−average LO)*100. Data (consisting of POC and inhibitor concentration in μM) is fitted to a 4-parameter equation (y=A+((B−A)/(1+((x/C)^D))), where A is the minimum y (POC) value, B is the maximum y (POC), C is the x (cpd concentration) at the point of inflection and D is the slope factor) using a Levenburg-Marquardt non-linear regression algorithm.

Of the compounds tested, exemplary compounds 1-2, 5, 6-22, 24-35, 28-46, 52, 54, 57-59 and 61 exhibited an average $IC_{50}$ value of 1.0 uM or less in the SCF stimulated UT7 proliferation and survival assay. The specific activities are provided herein.

Formulation and Modes of Administration/Methods of Use

For the treatment of C-kit mediated diseases including those listed herein, the compounds of the present invention may be administered by several different modes, including without limitation, oral, parental, by spray inhalation, rectal, or topical, as discussed herein. The term parenteral as used herein, includes subcutaneous, intravenous, intramuscular, intrasternal, infusion techniques or intraperitoneal administration.

Treatment of diseases and disorders herein is intended to also include therapeutic administration of a compound of the invention (or a pharmaceutical salt, derivative or prodrug thereof), or a pharmaceutical composition medicament comprising said compound, to a subject (i.e., to an animal, preferably a mammal, most preferably a human) believed to be in need of preventative treatment. Diseases or disorders which may be treated include, without limitation, allergies, mast cell related tumors and other c-kit mediated conditions. Treatment also encompasses administration of the compound, or a pharmaceutical composition comprising the compound, to subjects not having been diagnosed as having a need thereof, i.e., prophylactic administration to the subject. Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

"Treating" or "treatment of" within the context of the instant invention, means an alleviation, in whole or in part, of symptoms associated with a disorder or disease, or halt of further progression or worsening of those symptoms, or prevention or prophylaxis of the disease or disorder.

Similarly, as used herein, an "effective amount" or "therapeutically effective amount" of a compound of the invention refers to an amount of the compound, or pharmaceutical composition, that alleviates, in whole or in part, symptoms associated with a disorder or disease, or halts of further progression or worsening of those symptoms, or prevents or provides prophylaxis for the disease or disorder. For example, within the context of treating patients in need of an inhibitor of C-kit, successful treatment may include a reduction in mast cell mediated tumor; an alleviation of symptoms related to a fibrotic condition; or a halting in the progression of an allergic response.

While it may be possible to administer a compound of the invention alone, in the methods described, the compound administered is generally present as an active ingredient in a desired dosage unit formulation, such as pharmaceutically acceptable composition (also referred to as "medicament" herein) containing conventional pharmaceutically acceptable carriers. Thus, in another embodiment of the invention, there is provided a pharmaceutical composition comprising a compound of this invention in combination with a pharmaceutically acceptable carrier. Acceptable pharmaceutical carriers generally include diluents, excipients, adjuvants and the like as described herein.

A pharmaceutical composition of the invention may comprise an effective amount of a compound of the invention or an effective dosage amount (or unit dosage amount) of a compound of the invention. An effective dosage amount of a compound of the invention includes an amount less than, equal to, or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound may be administered by administering a portion of the composition.

The pharmaceutical compositions may generally be prepared by mixing one or more compounds of Formula I or II including stereoisomersor tautomers, solvates, pharmaceutically acceptable salts, derivatives or prodrugs thereof, with pharmaceutically acceptable carriers, excipients, binders, adjuvants, diluents and the like, to form a desired administrable formulation to treat or ameliorate a variety of disorders related to the activity of c-kit, particularly autoimmune disease.

Pharmaceutical compositions can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation.

Besides those representative dosage forms described herein, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (2000); and "Pharmaceutics The Science of Dosage Form Design, $2^{nd}$ Ed. (Aulton, ed.) Churchill Livingstone (2002). The following dosage forms are given by way of example and should not be construed as limiting the invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or stereoisomers, solvates, prodrugs, pharmaceutically acceptable salts or tautomers thereof, with at least one additive or excipient such as a starch or other additive and tableted, encapsulated or made into other desirable forms for conventional administration. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, and the like may be added for oral or parenteral administration.

For nasal administration, the pharmaceutical formulations may be a spray or aerosol containing an appropriate solvent and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms for parenteral administration generally include aqueous suspensions or oil suspensions, which may be prepared using a suitable dispersant or wetting agent and a suspending agent. Injectable forms may be in solution phase or a powder suitable for reconstitution as a solution. Both are prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is solid phase at room temperature but liquid phase at those temperatures suitable to release a drug inside the body, such as in the rectum. Various other agents and additives may be used in the preparation of suppositories as is well known to those of skill in the art.

The formulations of the invention may be designed to be short-acting, fast-releasing, long-acting, and sustained-releasing as described below. Thus, the pharmaceutical formulations may also be formulated for controlled release or for slow release. The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dosage amount or dose may vary depending upon the route of administration and dosage form. Typically, the compound or compounds of the instant invention are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The dosage regimen for treating C-kit mediated diseases with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

The pharmaceutical compositions may be subjected to conventional pharmaceutical operations such as sterilization and/or may contain conventional adjuvants, such as preservatives, stabilizers, wetting agents, emulsifiers, buffers etc. The pharmaceutically active compounds of this invention can be processed in accordance with conventional methods of pharmacy to produce medicinal agents for administration to patients, including humans and other mammals.

While the compounds of the present invention can be administered as the sole active pharmaceutical agent, they can also be used in combination with one or more compounds of the invention or with one or more other agents. When administered as a combination, the therapeutic agents can be formulated and given to the subject as a single composition or the combination of therapeutic agents can be formulated and given to the subject as separate compositions that are given at the same time or different times.

Treatment may also include administering the pharmaceutical formulations of the present invention in combination with other therapies. For example, the compounds and pharmaceutical formulations of the present invention may be administered before, during, or after surgical procedure and/or radiation therapy. Alternatively, the compounds of the invention can also be administered in conjunction with other anti-proliferative agents including those used in antisense and gene therapy.

The methods and compositions of the present invention may comprise a combination with another kinase inhibitor. Although the present invention is not limited to any particular kinase, kinase inhibitors contemplated for use include, without limitation, tyrphostin AG490 (2-cyano-3-(3,4-dihydroxyphenyl)-N-(benzyl)-2-propenamide), Iressa (ZD1839; Astra Zeneca); Gleevec (STI-571 or imatinib mesylate; Novartis); SU5416 (Pharmacia Corp./Sugen); and Tarceva (OSI-774; Roche/Genentech/OSI Pharmaceuticals).

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound having a Formula II

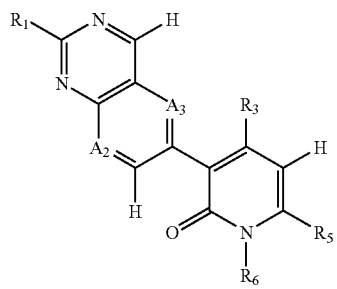

or a stereoisomer or pharmaceutically acceptable salt thereof, wherein
each of $A^2$ and $A^3$, independently, is CH;
$R^1$ is —$NR^7R^7$, —$NR^7R^8$, —$NR^9R^9$; or
$R^1$ is phenyl optionally substituted independently with 1-5 substituents of $R^9$;
$R^3$ is halo, haloalkyl, $C_{1-8}$alkyl or CN;
$R^5$ is H;

$R^6$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, dihydroindolyl, azaindolyl, isoindolyl, indazolyl, benzofuranyl, dihydrobenzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl or cyclohexyl, each of which is optionally substituted independently with 1-5 substituents of $R^9$;

$R^7$ is H, $C_{1-8}$-alkyl, $C_{2-8}$-alkenyl, $C_{2-8}$-alkynyl, $C_{3-8}$-cycloalkyl or $C_{4-8}$-cycloalkenyl, each of the $C_{1-8}$-alkyl, $C_{2-8}$-alkenyl, $C_{2-8}$-alkynyl, $C_{3-8}$-cycloalkyl and $C_{4-8}$-cycloalkenyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$ or $R^9$;

$R^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered ring of carbon atoms optionally including 1-3 heteroatoms selected from O, N, or S, and the ring optionally substituted independently with 1-3 substituents of $R^9$; and $R^9$ is H, halo, haloalkyl, CN, OH, $NO_2$, $NH_2$, acetyl, $C_{1-8}$-alkyl, $C_{2-8}$-alkenyl, $C_{2-8}$-alkynyl, $C_{3-8}$-cycloalkyl, $C_{4-8}$-cycloalkenyl, $C_{1-8}$alkylamino-, $C_{1-8}$-dialkylamino-, $C_{1-8}$-alkoxyl, $C_{1-8}$-thioalkoxyl or a ring selected from phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, dihydroindolyl, azaindolyl, isoindolyl, indazolyl, benzofuranyl, dihydrobenzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl and cyclohexyl, wherein each of the $C_{1-8}$alkyl, $C_{2-8}$-alkenyl, $C_{2-8}$-alkynyl, $C_{3-8}$-cycloalkyl, $C_{4-8}$-cycloalkenyl, $C_{1-8}$-alkylamino-, $C_{1-8}$-dialkylamino-, $C_{1-8}$-alkoxyl, $C_{1-8}$-thioalkoxyl and ring is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

2. A compound, or a pharmaceutically acceptable salt thereof, selected from:

1-(4-(1H-pyrrol-1-yl)phenyl)-3-(2-aminoquinazolin-6-yl)-4-methylpyridin-2(1H)-one;
3-(2-aminoquinazolin-6-yl)-1-(3-fluoro-4-methylphenyl)-4-methylpyridin-2(1H)-one;
3-(2-aminoquinazolin-6-yl)-1-(3-fluoro-4-methylphenyl)-4-methylpyridin-2(1H)-one;
3-(2-aminoquinazolin-6-yl)-4-methyl-1-(4-(oxazol-2-yl)phenyl)pyridin-2(1H)-one;
3-(2-aminoquinazolin-6-yl)-1-(3,5-dimethylphenyl)-4-methylpyridin-2(1H)-one;
3-(3-(2-aminoquinazolin-6-yl)-4-methyl-2-oxopyridin-1(2H)-yl)benzonitrile;
3-(2-aminoquinazolin-6-yl)-4-methyl-1-(2-(trifluoromethyl)-1H-benzo[d]imidazol-5-yl)pyridin-2(1H)-one;
3-(2-aminoquinazolin-6-yl)-1-(3-methoxy-5-(trifluoromethyl)phenyl)-4-methylpyridin-2(1H)-one;
3-(2-amino-6-quinazolinyl)-1-(4-(1,1-dimethylethyl)phenyl)-4-methyl-2(1H)-pyridinone;
3-(2-amino-6-quinazolinyl)-1-(3,4-dimethylphenyl)-4-methyl-2(1H)-pyridinone;
3-(2-amino-6-quinazolinyl)-4-methyl-1-(3-((trifluoromethyl)oxy)phenyl)-2(1H)-pyridinone;
3-(2-amino-6-quinazolinyl)-1-(3,3-dimethyl-2,3-dihydro-1H-indol-6-yl)-4-methyl-2(1H)-pyridinone;
3-(2-amino-6-quinazolinyl)-4-methyl-1-(6-quinolinyl)-2(1H)-pyridinone;
3-(2-amino-6-quinazolinyl)-1-(2,3-dihydro-1-benzofuran-5-yl)-4-methyl-2(1H)-pyridinone;
3-(2-amino-6-quinazolinyl)-4-methyl-1-(1H-indol-5-yl)-2(1H)-pyridinone;
1-(1-acetyl-3,3-dimethyl-2,3-dihydro-1H-indol-6-yl)-3-(2-amino-6-quinazolinyl)-4-methyl-2(1H)-pyridinone;
3-(2-amino-6-quinazolinyl)-4-methyl-1-(3-(trifluoromethyl)phenyl)-2(1H)-pyridinone;
3-(2-amino-6-quinazolinyl)-4-methyl-1-(3-(trifluoromethyl)phenyl)-2(1H)-pyridinone;
3-(2-amino-6-quinazolinyl)-1-(3-chlorophenyl)-4-methyl-2(1H)-pyridinone;
3-(2-amino-6-quinazolinyl)-4-methyl-1-(3-(methyloxy)phenyl)-2(1H)-pyridinone;
3-(2-amino-6-quinazolinyl)-4-methyl-1-phenyl-2(1H)-pyridinone;
3-(2-amino-6-quinazolinyl)-1-(1,5'-bi-1H-indol-5-yl)-4-methyl-2(1H)-pyridinone;
3-(2-aminoquinazolin-6-yl)-1-(4-isopropylphenyl)-4-methylpyridin-2(1H)-one;
1-(4-acetylphenyl)-3-(2-aminoquinazolin-6-yl)-4-methylpyridin-2(1H)-one;
ethyl 4-(3-(2-aminoquinazolin-6-yl)-4-methyl-2-oxopyridin-1(2H)-yl)benzoate;
3-(2-aminoquinazolin-6-yl)-4-methyl-1-(4-(trifluoromethyl)phenyl)pyridin-2(1H)-one;
3-(2-aminoquinazolin-6-yl)-1-(4-methoxyphenyl)-4-methylpyridin-2(1H)-one;
3-(2-aminoquinazolin-6-yl)-1-(4-chlorophenyl)-4-methylpyridin-2(1H)-one;
3-(2-aminoquinazolin-6-yl)-1-(4-fluorophenyl)-4-methylpyridin-2(1H)-one;
3-(2-aminoquinazolin-6-yl)-4-methyl-1-(4-morpholinophenyl)pyridin-2(1H)-one;
3-(2-aminoquinazolin-6-yl)-4-methyl-1-(4-(morpholinomethyl)phenyl)pyridin-2(1H)-one;
tert-butyl 4-(4-(3-(2-aminoquinazolin-6-yl)-4-methyl-2-oxopyridin-1(2H)-yl)phenyl)piperazine-1-carboxylate;
ethyl 2-(4-(3-(2-aminoquinazolin-6-yl)-4-methyl-2-oxopyridin-1(2H)-yl)phenylamino)acetate;
1-(4-(1H-pyrazol-1-yl)phenyl)-3-(2-aminoquinazolin-6-yl)-4-methylpyridin-2(1H)-one;
3-(2-aminoquinazolin-6-yl)-1-(3,4-difluorophenyl)-4-methylpyridin-2(1H)-one;
3-(2-aminoquinazolin-6-yl)-1-(3,4-dichlorophenyl)-4-methylpyridin-2(1H)-one;
3-(2-aminoquinazolin-6-yl)-1-(3-chloro-4-methylphenyl)-4-methylpyridin-2(1H)-one;
3-(2-aminoquinazolin-6-yl)-1-(4-fluoro-3-methylphenyl)-4-methylpyridin-2(1H)-one;
3-(2-aminoquinazolin-6-yl)-1-(4-fluoro-3-(trifluoromethyl)phenyl)-4-methylpyridin-2(1H)-one;
3-(2-aminoquinazolin-6-yl)-1-(4-chloro-3-fluorophenyl)-4-methylpyridin-2(1H)-one;
3-(2-aminoquinazolin-6-yl)-1-(3-chloro-4-fluorophenyl)-4-methylpyridin-2(1H)-one; and
3-(2-aminoquinazolin-6-yl)-1-(3,5-dichlorophenyl)-4-methylpyridin-2(1H)-one.

3. A pharmaceutical composition comprising a pharmaceutically acceptable carrier and a compound according to claim 1.

4. A pharmaceutical composition comprising a pharmaceutically acceptable carrier and a compound according to claim 2.

* * * * *